US 6,544,265 B2

(12) United States Patent  
Lieberman

(10) Patent No.: US 6,544,265 B2
(45) Date of Patent: *Apr. 8, 2003

(54) APPARATUS FOR IMPLANTATION INTO BONE RELATED APPLICATIONS

(75) Inventor: Isador H. Lieberman, Pepper Pike, OH (US)

(73) Assignee: The Cleveland Clinic Foundation, Cleveland, OH (US)

(*) Notice: Subject to any disclaimer, the term of this patent is extended or adjusted under 35 U.S.C. 154(b) by 67 days.

This patent is subject to a terminal disclaimer.

(21) Appl. No.: 09/781,847

(22) Filed: Feb. 14, 2001

(65) Prior Publication Data

US 2002/0055737 A1 May 9, 2002

Related U.S. Application Data

(63) Continuation-in-part of application No. 09/708,940, filed on Nov. 8, 2000, and a continuation-in-part of application No. 09/708,292, filed on Nov. 8, 2000, now Pat. No. 6,468,309.

(51) Int. Cl.[7] .............................................. A61B 17/56
(52) U.S. Cl. .......................................... 606/69; 606/61
(58) Field of Search .............................. 606/61, 69, 71, 606/72, 73

(56) References Cited

U.S. PATENT DOCUMENTS

| 2,033,039 | A |   | 3/1936 | Limpert ...................... 24/710.9 |
| 4,762,453 | A |   | 8/1988 | DeCaro ........................ 411/383 |
| 4,854,311 | A |   | 8/1989 | Steffee ........................... 606/66 |
| 4,961,740 | A |   | 10/1990 | Ray et al. ..................... 606/61 |
| 5,055,104 | A |   | 10/1991 | Ray ............................... 606/61 |
| 5,263,953 | A |   | 11/1993 | Bagby .......................... 606/61 |
| 5,437,266 | A | * | 8/1995 | McPherson et al. ........ 606/217 |
| 5,534,031 | A |   | 7/1996 | Matsuzaki et al. ............ 623/17 |
| 5,582,616 | A |   | 12/1996 | Bolduc et al. ............... 606/143 |

(List continued on next page.)

FOREIGN PATENT DOCUMENTS

| EP | 0374088 A1 | 6/1990 |
| EP | 0663184 A1 | 7/1995 |
| FR | 2299548 | 8/1976 |
| SU | 1071297 A | 2/1984 |
| WO | WO0224087 A1 | 3/2002 |

OTHER PUBLICATIONS

"Anterior Vertebralbody Screw Pullout Testing, A Comparison of Zielke, Kaneda, Universal Spine System, and Universal Spine System with Pullout–Resistant Nut", by Isador H. Lieberman et al., reprinted from SPINE, vol. 23, No. 8, Apr. 15, 1998.

Primary Examiner—John J. Wilson
(74) Attorney, Agent, or Firm—Tarolli, Sundheim, Covell & Tummino L.L.P.

(57) ABSTRACT

An apparatus (10) is provided for implantation into a bone (12) in a patient's spine or pelvis. The apparatus (10) comprises a platform (24) having a first surface (38) for facing the bone (12). The platform (24) includes structure (32, 34, 36) for connection to a spinal fixation implant (100). The apparatus (10) further comprises helical spikes (50, 52) for embedding into the bone (12) upon rotation of the platform (24). The helical spikes (50, 52) project tangentially from the platform (24) and extend around a longitudinal axis (22). The helical spikes (50, 52) have a tip portion (58) which penetrates into the bone (12) as the platform (24) is rotated. The helical spikes (50, 52) further have a connecting portion (54) connected to the platform (24) and an intermediate portion (56) extending between the connecting portion and the tip portion (58). At least one of the intermediate portion (56) and the connecting portion (54) has a tubular cross-section.

40 Claims, 11 Drawing Sheets

U.S. PATENT DOCUMENTS

| | | | |
|---|---|---|---|
| 5,626,613 A | 5/1997 | Schmieding | 606/232 |
| 5,662,683 A | 9/1997 | Kay | 606/232 |
| 5,728,116 A | 3/1998 | Rosenman | 606/151 |
| 5,800,550 A | 9/1998 | Sertich | 623/17 |
| 5,810,851 A | 9/1998 | Yoon | 606/148 |
| 5,824,008 A | 10/1998 | Bolduc et al. | 606/43 |
| 5,888,223 A | 3/1999 | Bray, Jr. | 623/17 |
| 5,904,696 A | 5/1999 | Rosenman | 606/151 |
| 6,010,502 A | 1/2000 | Bagby | 606/61 |
| 6,036,701 A | 3/2000 | Rosenman | 606/151 |
| 6,071,310 A | 6/2000 | Picha et al. | 623/17 |
| 6,080,155 A | 6/2000 | Michelson | 606/61 |
| 6,102,950 A | 8/2000 | Vaccaro | 623/17 |
| 6,106,557 A | 8/2000 | Robioneck et al. | 623/17 |
| 6,113,638 A | 9/2000 | Williams et al. | 623/17 |
| 6,120,502 A | 9/2000 | Michelson | 606/61 |
| 6,120,503 A | 9/2000 | Michelson | 606/61 |
| 6,123,705 A | 9/2000 | Michelson | 606/61 |
| 6,126,688 A | 10/2000 | McDonnell | 623/17.16 |
| 6,126,689 A | 10/2000 | Brett | 623/17.16 |
| 6,206,882 B1 * | 3/2001 | Cohen | 606/69 |
| 6,296,656 B1 | 10/2001 | Bolduc et al. | 606/213 |

* cited by examiner

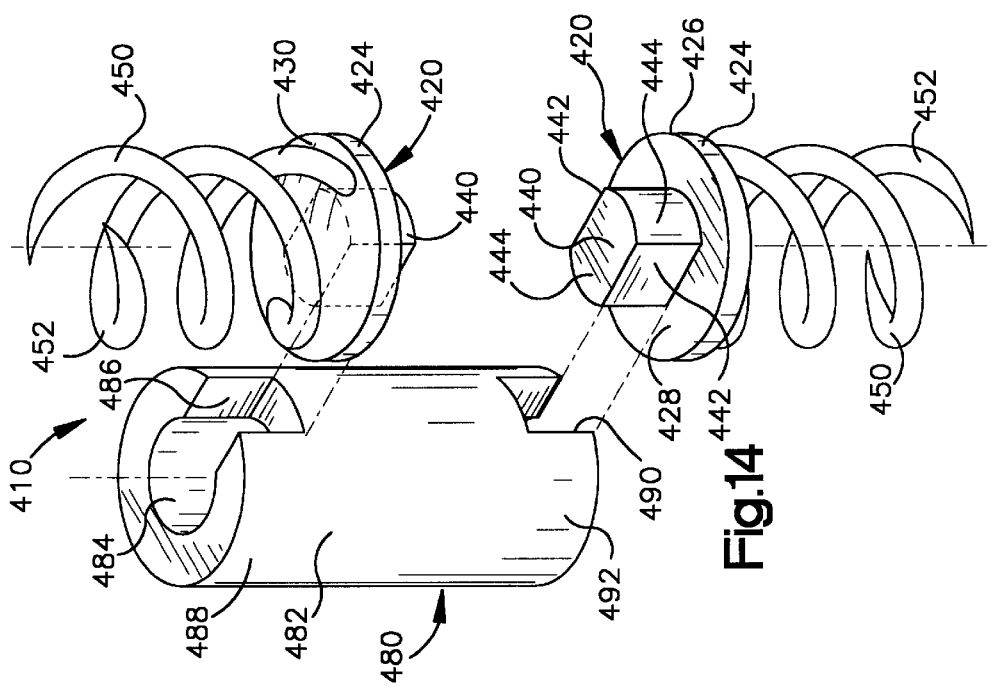
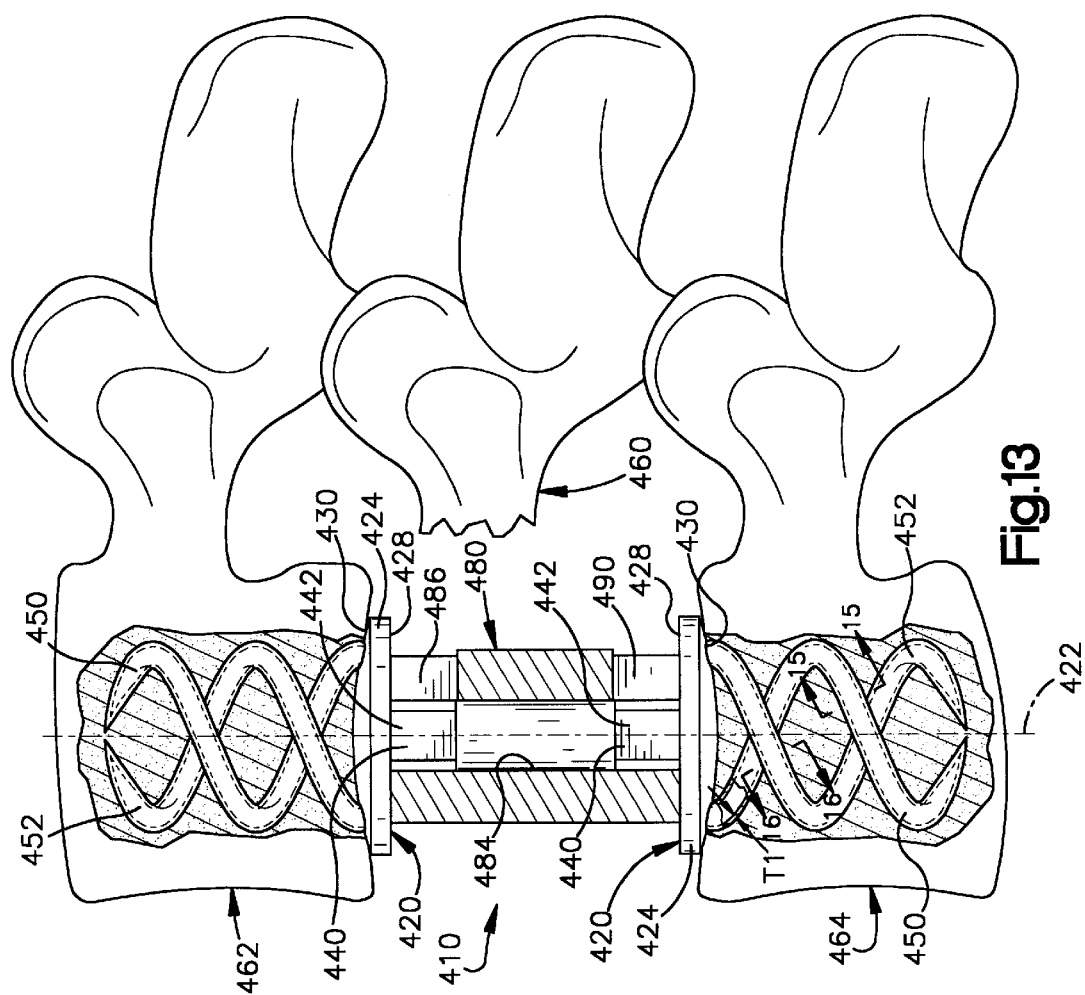

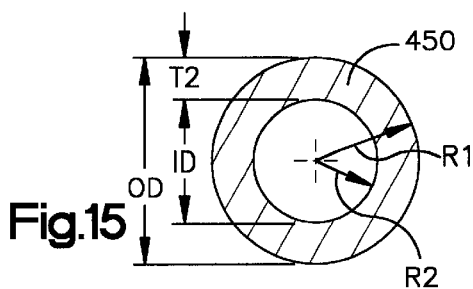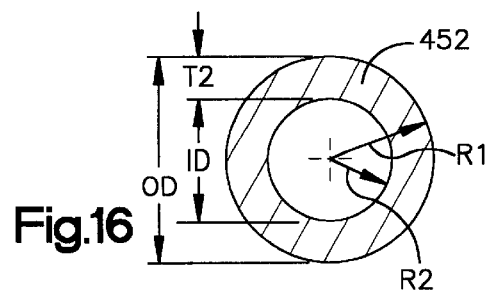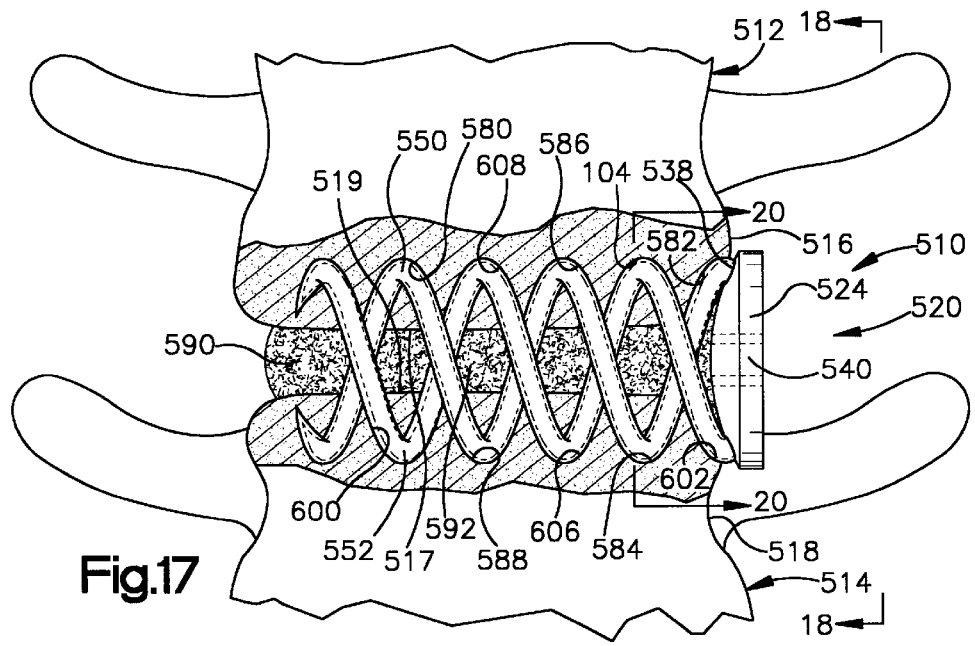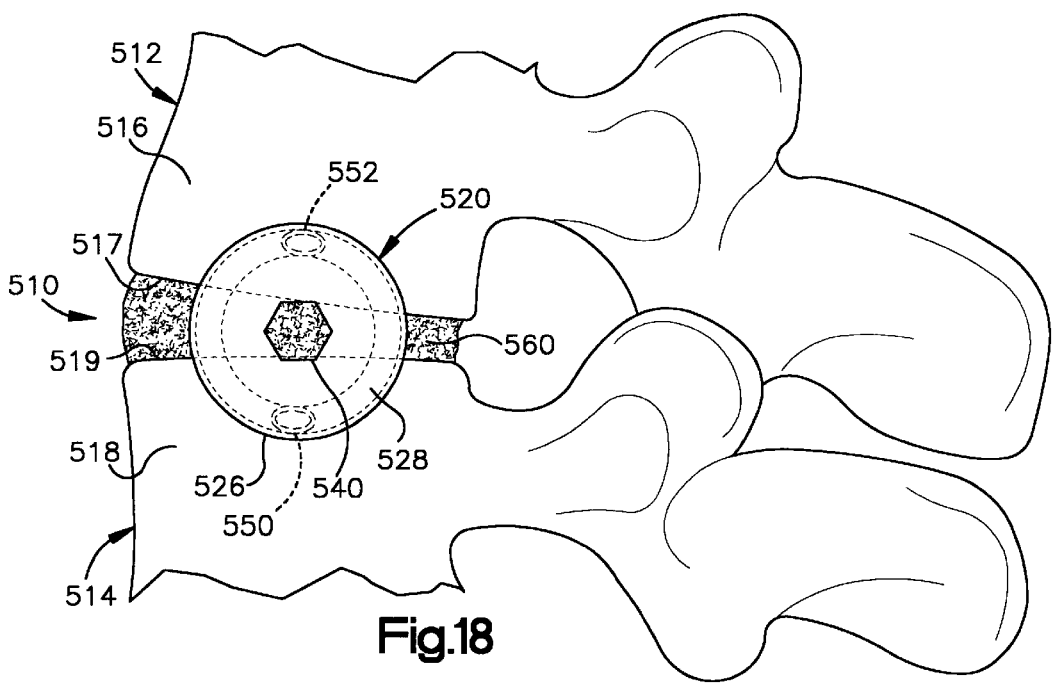

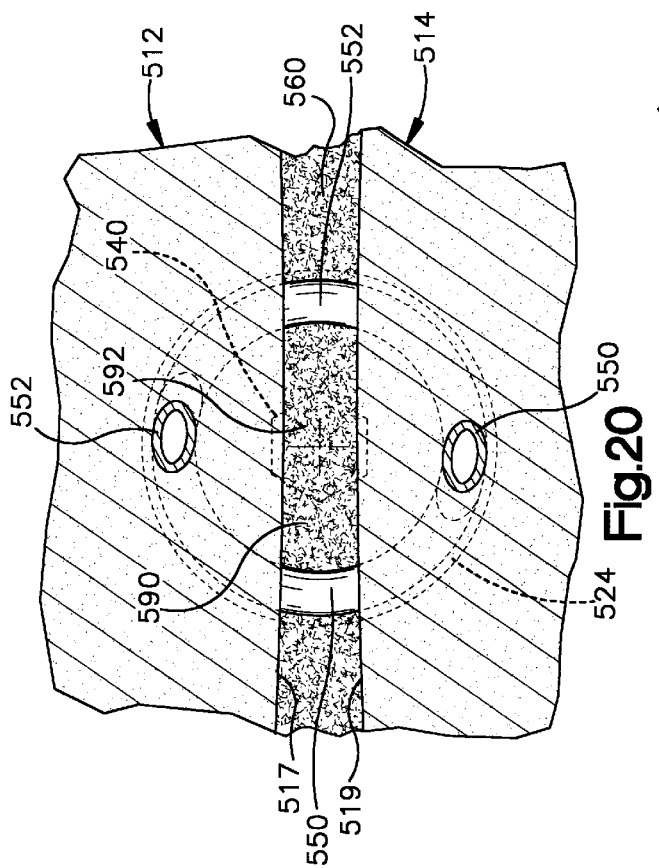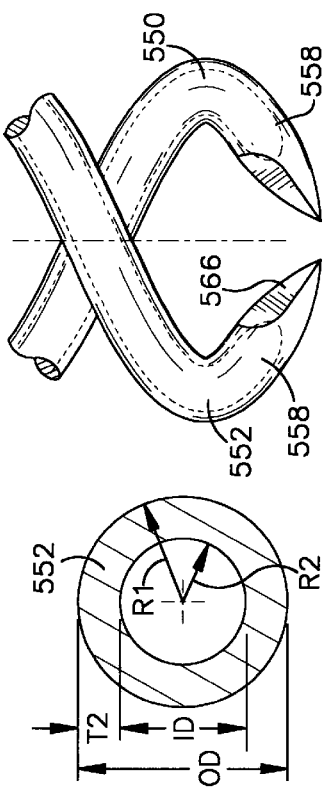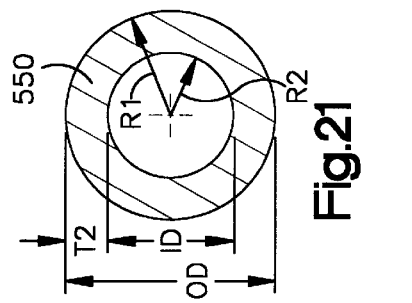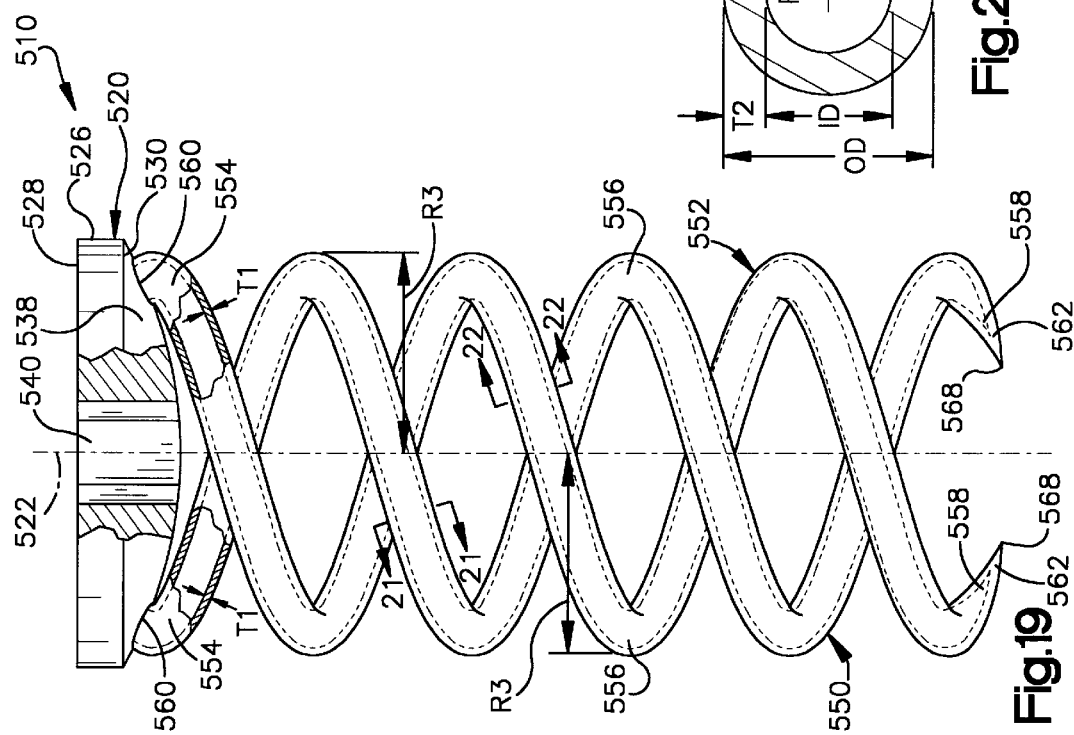

APPARATUS FOR IMPLANTATION INTO BONE RELATED APPLICATIONS

RELATED APPLICATIONS

This application is a continuation-in-part of U.S. patent application Ser. No. 09/708,940, filed Nov. 8, 2000, and U.S. patent application Ser. No. 09/708,292, also filed on Nov. 8, 2000, now U.S. Pat. No. 6,468,309. The entire subject matter of the aforementioned two co-pending applications is incorporated herein by reference.

TECHNICAL FIELD

The present invention is directed to an apparatus for implantation into a bone in a patient's spine or pelvis, and is particularly directed to an apparatus that, when implanted, is resistant to toggling in the bone and to being pulled from the bone. The present invention is also directed to an apparatus for attaching and stabilizing adjacent vertebral bodies while the vertebral bodies fuse together.

BACKGROUND OF THE INVENTION

Bone screws are used in the medical field for a variety of purposes. Typical uses for bone screws, also referred as bone anchors, include treating a bone fracture, attaching a corrective device to parts of a fractured bone in an area adjacent to the fracture, and attaching a corrective device to a group of bones, such as vertebrae of a spinal column.

Most known bone screws use a conventional screw design, i.e. a solid shank, with one or more external thread convolutions. The solid shank and external threads of the conventional bone screws can cause the bone screws to displace an undesirably large amount of bone when implanted. Further, such conventional bone screws require a large amount of torque to implant the screw into a vertebral body.

It is also known to use a corkscrew-style helical spike as a tissue anchor. The known corkscrew-style tissue anchors, when implanted, displace less bone than the conventional bone screws, but are generally not able to withstand high tensile loads without structural failure. European Patent No. 0 374 088 A1 discloses a bone screw having a twin-corkscrew design. In this twin-corkscrew design, which is formed by drilling a passage up through a screw having a solid shank and then machining out the material between the two corkscrews, the junction of the corkscrews with the shank is unlikely to be capable of structurally withstanding high tensile loads and repetitive fatigue loads. This structural weakness in the design of the screw in the EP 0 374 088 document is further compounded by the corkscrews having a larger overall diameter than the head of the screw where torque is applied.

One of the more challenging applications of a bone screw is implantation of the screw into the cancellous bone of a patient's spine or pelvis. For example, bone screws are frequently implanted into the cancellous bone of a patient's lumbar vertebrae during a spinal fixation procedure to correct scoliosis. Once implanted, the bone screws are used to mount suitable spinal fixation instrumentation, such as clamps, rods, and plates. Unfortunately, many of the known bone screws, such as those described above, can be susceptible to toggling in the vertebral body and can also pull out of the vertebral body due to the substantial forces on the screws from human body movement and muscle memory. In order to achieve a high pull-out resistance, it is known to thread a bone screw all of the way through a vertebrae and place a nut on the opposite side. However, use of such a nut increases the complexity of the surgical procedure.

Hence, it is desirable to provide an apparatus for implantation into a bone in a patient's spine or pelvis in a minimally invasive endoscopic procedure with a reduced amount of insertion torque required. The desirable apparatus would provide a platform for connecting spinal fixation instrumentation and, when implanted, be highly resistant to toggling in the bone and to being pulled out of the bone despite the substantial forces on the apparatus from human body movement and muscle memory.

Another application for an anchor or fastening-type apparatus in the field of spine surgery is the stabilization of adjacent vertebrae. Each adjacent pair of vertebrae in the human spinal column are separated by an intervertebral disc that makes relative movement of the vertebrae possible. Problems, however, can develop with one or more of the discs, causing severe back pain. In some cases, it is necessary to remove a problematic disc and to fuse the adjacent vertebrae together in order to relieve pain.

One known method for fusing an adjacent pair of vertebrae following removal of a disc is to implant a device, commonly referred to as a fusion cage, into the interbody space where the disc was removed. The fusion cage facilitates fusion of the vertebrae. Typically, procedures such as reaming and/or tapping of adjacent vertebrae are required to prepare the adjacent vertebrae to receive the fusion cage. Such procedures normally involve substantial cutting of the hard cortical bone of the end plates of the adjacent vertebrae, which can weaken the end plates and lead to collapse of the vertebrae. The fusion cage is then positioned in the interbody space and into engagement with the adjacent vertebrae. At least one known fusion cage has relatively movable parts that enable the fusion cage to be expanded after the fusion cage is positioned in the interbody space between adjacent vertebrae. The design of this expandable fusion cage is, however, relatively complex.

Typically, a fusion cage includes an internal cavity that is filled with bone graft material. The fusion cage and the bone graft material promote bone growth that slowly unites the adjacent vertebrae. The typical fusion cage, while in engagement with the adjacent vertebrae, does not attach to the vertebrae and thus does not resist relative movement of the vertebrae, through bending or rotation, along any one of the three planes of motion (sagittal, coronal, or horizontal). Rather, the typical fusion cage relies on the viscoelasticity of the surrounding ligaments to stabilize the adjacent vertebrae.

It is desirable to provide an apparatus for implantation into an adjacent pair of vertebral bodies that attaches to and thus fastens the vertebral bodies while they fuse together despite the forces on the apparatus from human body movement and muscle memory. It is further desirable to provide an apparatus which has a reduced insertion torque requirement, a simple one-piece construction, and which may be implanted into an adjacent pair of vertebrae without having to prepare the adjacent vertebrae to accept the apparatus by substantial cutting of the cortical bone.

SUMMARY OF THE INVENTION

The present invention is an apparatus for implantation into a bone in a patient's spine or pelvis. The apparatus, when implanted, is resistant to toggling in the bone and to being pulled from the bone. The apparatus comprises a platform having a first surface for facing a bone in a patient's spine or pelvis. The platform includes structure for connection to a spinal fixation implant. The apparatus further comprises at least one helical spike for embedding into the bone upon rotation of the platform. The at least one helical spike projects tangentially from the platform and extends around a longitudinal axis. The at least one helical spike has a tip portion at a distal end which penetrates into the bone as the platform is rotated. The at least one helical spike further has a connecting portion at a proximal end connected to the platform and an intermediate portion extending between the connecting portion and the tip portion. At least one of the intermediate portion and the connecting portion of the at least one helical spike has a tubular cross-section defined by an outer diameter and an inner diameter of the at least one helical spike.

In accordance with another embodiment, the present invention is an apparatus comprising at least one anchor for implantation into a bone. The anchor, when implanted, is resistant to toggling in the bone and to being pulled from the bone. The apparatus further comprises a spinal fixation implant for extending between and connecting a plurality of bones. The anchor includes a platform having a first surface for facing the bone. The platform further has structure for connection with the spinal fixation implant. The anchor further includes at least two helical spikes for embedding into the bone upon rotation of the platform. The at least two helical spikes are spaced apart and project tangentially from the first surface on the platform. The at least two helical spikes extend around a longitudinal axis. Each of the at least two helical spikes has a tip portion at a distal end which penetrates into the bone as the platform is rotated. Each of the at least two helical spikes further has a connecting portion at a proximal end that is connected to the platform, and an intermediate portion extending between the connecting portion and the tip portion. At least one of the intermediate portion and the connecting portion of each of the at least two helical spikes has a tubular cross-section defined by an outer diameter and an inner diameter of the at least two helical spikes.

In accordance with yet another embodiment, the present invention comprises an apparatus for implantation into an adjacent pair of vertebral bodies having first and second surfaces that oppose each other. The apparatus, when implanted, is attached to the adjacent pair of vertebral bodies and stabilizes the vertebral bodies while the vertebral bodies fuse together. The apparatus comprises a platform having a third surface extending transverse to the first and second surfaces. The apparatus further comprises at least one helical spike for embedding into each of the adjacent pair of vertebral bodies upon rotation of the platform to attach the at least one helical spike to each of the vertebral bodies and thus fasten (pin) the vertebral bodies together. The at least one helical spike projects from the platform and extends around a longitudinal axis. The at least one helical spike has a tip portion at a distal end for penetrating the first and second surfaces and for screwing into the adjacent pair of vertebral bodies as the platform is rotated. At least a portion of the at least one spike has a tubular cross-section defined by an outer diameter and an inner diameter. The at least one helical spike at least partially defines an internal cavity for receiving material that promotes fusion of the vertebral bodies.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 13 is a schematic view, partially in section, of a third embodiment of the present invention;

FIG. 14 is an exploded perspective view of the apparatus of FIG. 13;

FIG. 15 is a sectional view taken along line 15—15 in FIG. 13;

FIG. 16 is a sectional view taken along line 16—16 in FIG. 13;

FIG. 17 is a schematic anterior view of an apparatus implanted in an adjacent pair of vertebral bodies in accordance with a fourth embodiment of the present invention;

FIG. 18 is an end view taken along line 18—18 in FIG. 17;

FIG. 19 is a side view of the apparatus of FIG. 17;

FIG. 20 is a sectional view taken along 20—20 in FIG. 17;

FIG. 21 is a sectional view taken along 21—21 in FIG. 19;

FIG. 22 is a sectional view taken along 22—22 in FIG. 19;

FIG. 23 illustrates an alternate configuration for an end portion of the apparatus of FIG. 19;

DESCRIPTION OF PREFERRED EMBODIMENTS

The present invention is directed to an apparatus for implantation into a bone in a patient's spine or pelvis, and is particularly directed to an apparatus that, when implanted, is resistant to toggling in the bone and to being pulled from the bone. The present invention is also directed to an apparatus for attaching and stabilizing adjacent vertebral bodies while the vertebral bodies fuse together.

Figure 1:
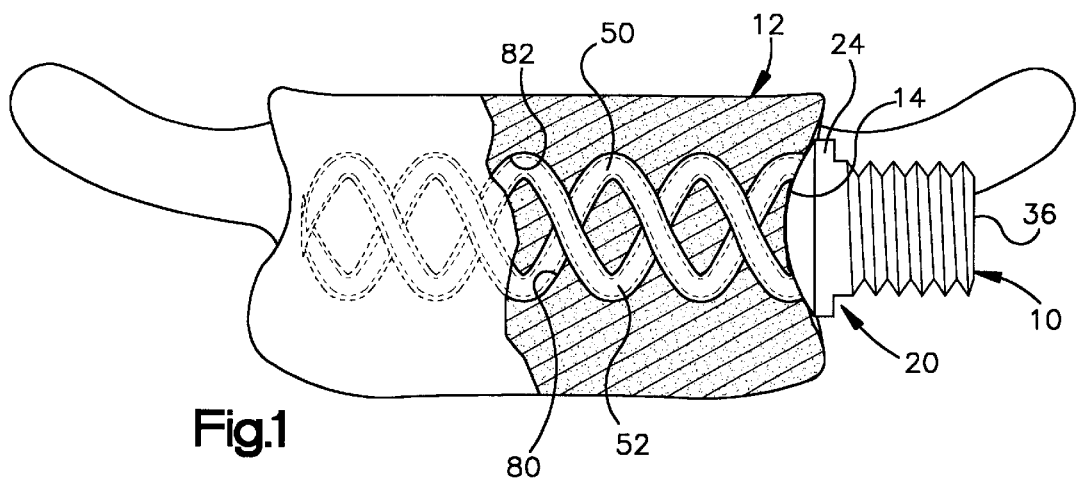
FIG. 1 is a schematic anterior view of an apparatus constructed in accordance with the present invention implanted in a vertebral body.

As representative of the present invention, FIG. 1 illustrates an apparatus 10 implanted in a lumbar vertebrae 12. It should be understood that the apparatus 10 could be implanted into any vertebral body, including the sacrum. The lumbar vertebrae 12 has a concave side surface 14.

The apparatus 10 comprises an anchor 20 made from a biocompatible material, such as titanium or stainless steel. It is contemplated that the biocompatible material used for the anchor 20 could be polymeric or composite (i.e., carbon fiber or other biologic composite) in nature. It is further contemplated that the biocompatible material used to make the anchor 20 could also be biodegradable.

Figure 3:
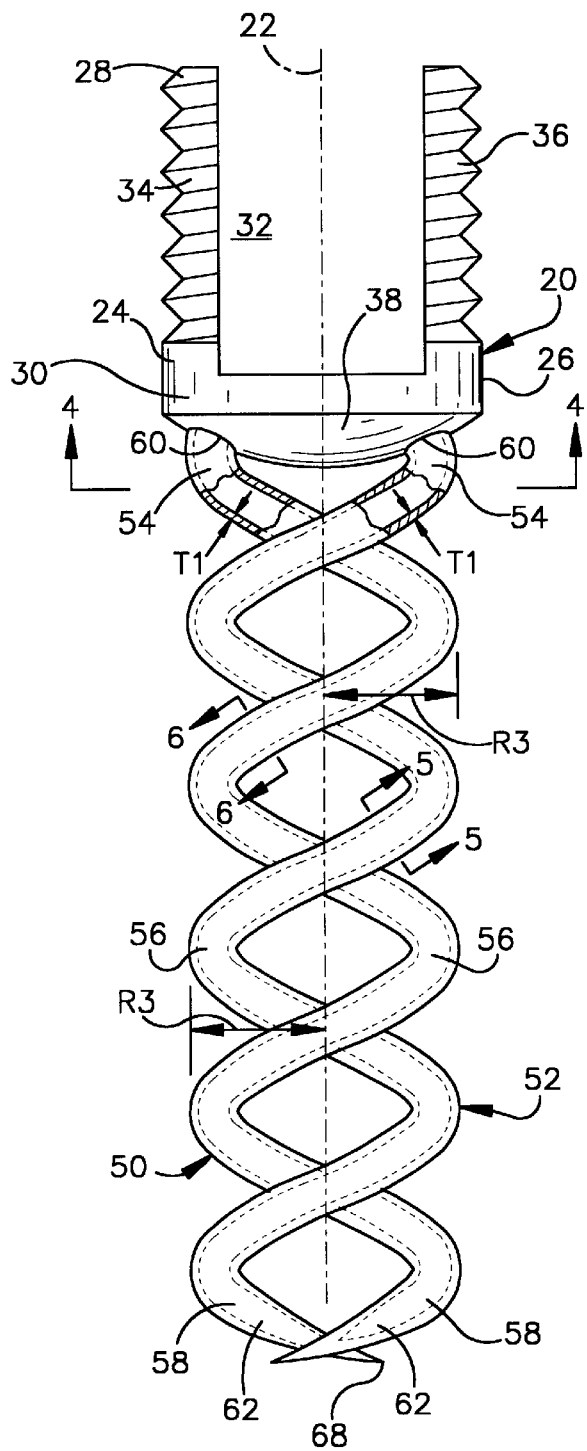
FIG. 3 is a side view of the apparatus of FIG. 1.

The anchor 20 is centered about a longitudinal axis 22 (FIG. 3). The anchor 20 includes a platform 24 having a generally cylindrical outer surface 26 extending between oppositely disposed first and second ends 28 and 30 of the platform. The platform 24 includes a generally rectangular slot 32 that extends axially from the first end 28 toward the second end 30 of the platform. Adjacent the first end 28, the outer surface 26 of the platform 24 includes first and second segments of external threads 34 and 36 that are separated by the slot 32. The slot 32 and the threads 34 and 36 provide structure for connecting spinal fixation instrumentation to the platform 24 as discussed further below. The second end 30 of the platform 24 includes an end surface 38 having a convex shape that is complimentary to the shape of the concave side surface 14 of the vertebrae 12. The end surface 38 of the platform 24 may include barbs (not shown) or other suitable structure for fixedly engaging the side surface 14 of the vertebrae 12. Further the end surface 38 of the platform 24 may also be porous, pitted, or have a biocompatible surface coating to assist with fixation of the anchor 20 to the vertebrae 12.

Figure 5:
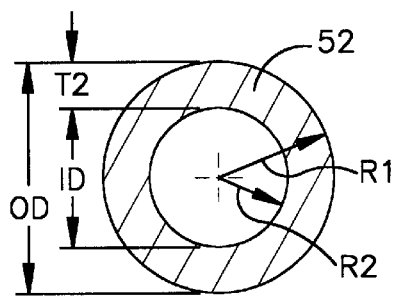
FIG. 5 is a sectional view taken along 5—5 in FIG. 3.
Figure 6:
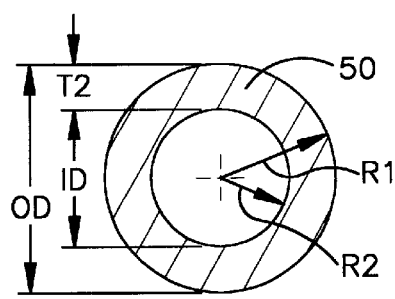
FIG. 6 is a sectional view taken along 6—6 in FIG. 3.

First and second helical spikes 50 and 52 project tangentially from the end surface 38 of the platform 24. The helical spikes 50 and 52 resemble a pair of intertwined corkscrews. As shown in FIGS. 5 and 6, each of the helical spikes 50 and 52 has a tubular cross-section defined by an outer diameter OD and an inner diameter ID. The outer diameter OD of each of the helical spikes 50 and 52 has a first radius R1 and the inner diameter ID of each of the helical spikes has a second radius R2 that is less than the first radius R1.

According to the embodiment illustrated in FIGS. 1–6, the first and second helical spikes 50 and 52 extend around the axis 22. The spikes 50 and 52 extend in a helical pattern about the axis 22 at the same, constant overall radius R3 (FIG. 3). It is contemplated, however, that the first and second helical spikes 50 and 52 could extend about the axis 22 at different radiuses. Further, it is contemplated that the radius of one or both of the first and second helical spikes 50 and 52 could increase or decrease as the helical spikes extend away from the platform 24. In order for the anchor 20 to be implanted endoscopically through a typical cannula (not shown), the platform 24 and the helical spikes 50 and 52 should be less than 20 mm in overall diameter. It should be understood that the anchor 20 could have an overall diameter that is greater than 20 mm for certain applications, and that the anchor could be also implanted in an open surgical procedure.

In the illustrated embodiment of FIGS. 1–6, the first and second helical spikes 50 and 52 have the same axial length, and also have the same tubular cross-sectional shape. It is contemplated, however, that the first and second helical spikes 50 and 52 could have different axial lengths. Further, it is contemplated that the helical spikes 50 and 52 could have a different cross-sectional shape, such as an oval shape. It also contemplated that the first and second helical spikes 50 and 52 could have different outer diameters (i.e., one spike being thicker than the other spike). Finally, it is contemplated that the helical spikes 50 and 52 should have the same pitch, and that the pitch of the helical spikes would be selected based on the specific surgical application and quality of the bone in which the anchor 20 is to be implanted.

Each of the first and second helical spikes 50 and 52 can be divided into three portions: a connecting portion 54, an intermediate portion 56, and a tip portion 58. The connecting portion 54 of each of the helical spikes 50 and 52 is located at a proximal end 60 that adjoins the end surface 38 of the platform 24. The connecting portion 54 may include barbs (not shown) for resisting pull-out of the helical spikes 50 and 52 from the vertebrae 12. According to one method for manufacturing the anchor 20, the connecting portion 54 of each of the helical spikes 50 and 52 is fixedly attached to the platform 24 by inserting, in a tangential direction, the proximal ends 60 of the helical spikes into openings (not shown) in the end surface 38 and welding the connecting portions 54 to the platform. The inserted proximal ends 60 of the helical spikes 50 and 52 help to reduce tensile bending stresses on the helical spikes under tensile (or pull-out) loads.

Alternatively, the helical spikes 50 and 52 may be formed integrally with the platform 24, such as by casting the anchor 20. If the anchor 20 is cast, it is contemplated that a fillet (not shown) may be added at the junction of the helical spikes 50 and 52 and the platform 24 to strengthen the junction and minimize stress concentrations at the connecting portions 54. The fillet at the junction of the helical spikes 50 and 52 and the platform 24 also helps to reduce bending stresses in the connection portions 54 of the helical spikes under tensile (or pull-out) loads.

Figure 4:
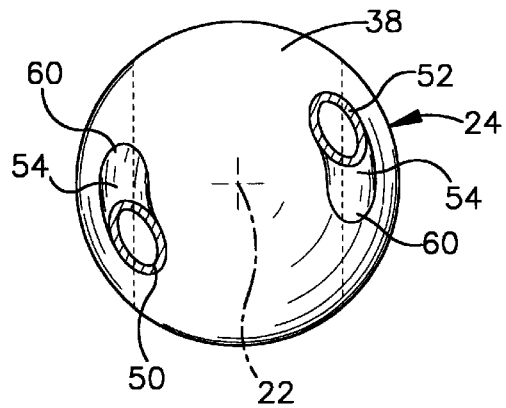
FIG. 4 is a sectional view taken along 4—4 in FIG. 3.

As best seen in FIG. 4, the connecting portions 54 at the proximal ends 60 of the first and second helical spikes 50 and 52 are spaced 180° apart about the axis 22 to balance the anchor 20 and evenly distribute loads on the helical spikes. The connecting portion 54 of each of the helical spikes 50 and 52 has a first wall thickness T1 (FIG. 3) defined between the first radius R1 and the second radius R2.

The tip portion 58 of each of the helical spikes 50 and 52 is located at a distal end 62 of the helical spikes. The intermediate portion 56 of each of the helical spikes 50 and 52 extends between the tip portion 58 and the connecting portion 54. The intermediate portion 56 and the tip portion 58 of each of the helical spikes 50 and 52 have an outer diameter that is less than or equal to the outer diameter of the connecting portions 54. If the outer diameter of the intermediate portion 56 and the tip portion 58 is less than the outer diameter of the connecting portion 54 of each of the helical spikes 50 and 52, the increased thickness of the connecting portions will help to provide the anchor 20 with increased tensile strength at the junction of the helical spikes and the platform 24.

The intermediate portion 56 of each of the helical spikes 50 and 52 has a second wall thickness T2 (FIGS. 5 and 6)

defined between the first radius R1 and the second radius R2. The second wall thickness T2 of the intermediate portion 56 is less than or equal to the first wall thickness T1 of the connecting portion 54. If the first wall thickness T1 is greater than the second wall thickness T2, the additional wall thickness in the connecting portions 54 of the helical spikes 50 and 52 will help to increase the tensile strength of the anchor 20.

It is contemplated that the tip portions 58 of the helical spikes 50 and 52 will have a wall thickness (not numbered) that is greater than or equal to the wall thickness T2 of the intermediate portions 56. Additional wall thicknesses in the tip portions 58 will provide additional strength that may be beneficial during the initial stages of implantation of the anchor 20.

It is further contemplated that the wall thicknesses T1 and T2 of each of the helical spikes 50 and 52 may be varied, and selected, depending on the specific application for the anchor 20. By varying the wall thickness, the wall thickness can be selected to match the modulus of elasticity of the bone, which can improve fixation strength and load-sharing characteristics of the anchor 20 and the bone.

Figure 30:
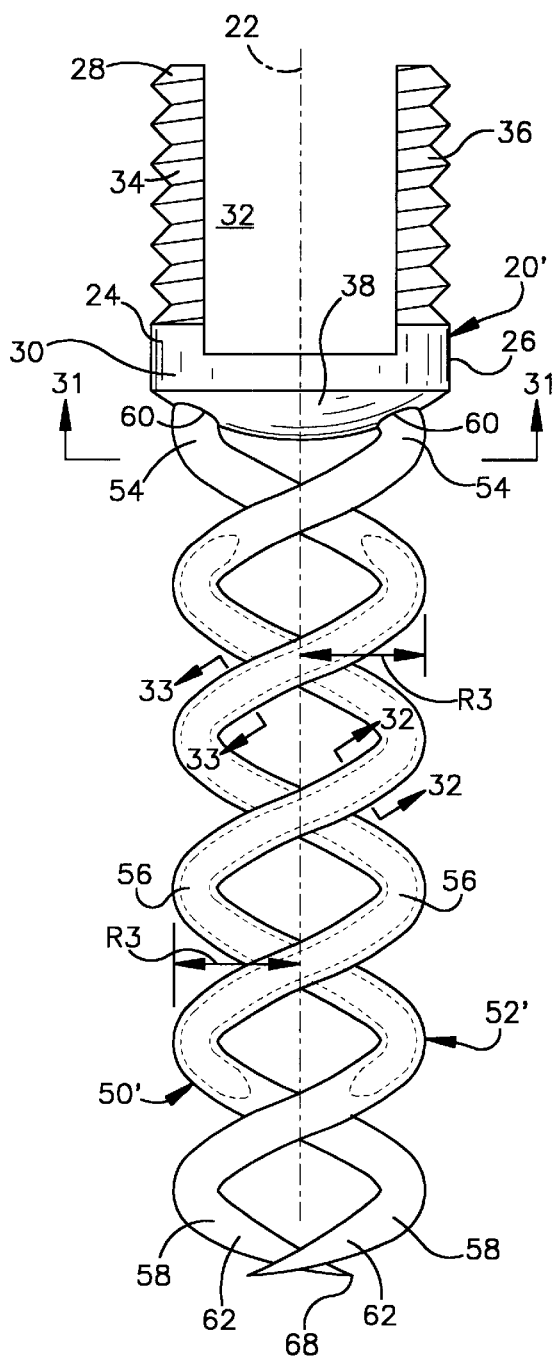
FIG. 30 is a side view, similar to FIG. 3, illustrating modification to the present invention.
Figure 31:
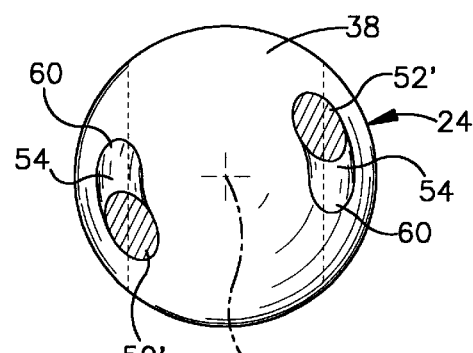
FIG. 31 is a sectional view taken along line 31—31 in FIG. 30.
Figure 32:
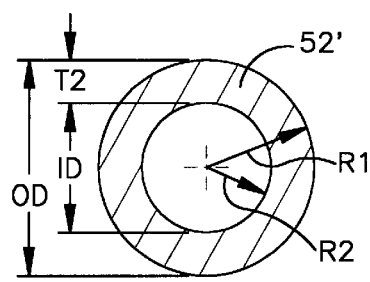
FIG. 32 is a sectional view taken along line 32—32 in FIG. 30.
Figure 33:
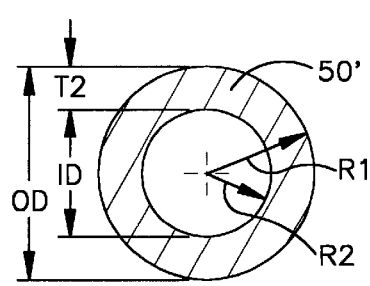
FIG. 33 is a sectional view taken along line 33—33 in FIG. 30.

FIGS. 30–33 illustrate modified configurations for the helical spikes 50 and 52 in accordance with the present invention. As shown in FIG. 30, an anchor 20' has helical spikes 50' and 52'. FIGS. 30–33 illustrate that the connecting portions 54 and/or the tip portions 58 of the helical spikes 50' and 52' could have a solid cross-section, while the intermediate portions 56 have a tubular cross-section. Such modified configurations of the anchor 20' provide additional means for matching the modulus of elasticity of the bone. The aforementioned variations in the configuration of the anchors 20, 20' allow the surgeon to select a particular configuration based on the specific surgical application and quality of the bone in which the anchor is to be implanted.

Figure 7:
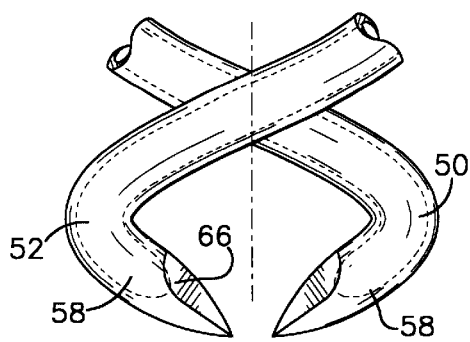
FIG. 7 illustrates an alternate configuration for an end portion of the apparatus of FIG. 1.

The tip portion 58 of each of the helical spikes 50 and 52 illustrated in FIGS. 1–6 has an elongated conical shape with a sharp pointed tip 68 for penetrating into the vertebrae 12 as the platform 24 of the anchor 20 is rotated in a clockwise direction. FIG. 7 illustrates an alternative, self-tapping configuration for the tip portions 58 which includes a planar surface 66 for driving into the vertebrae 12, in the same manner that a wood chisel turned upside-down drives into wood, as the platform 24 is rotated. It is contemplated that the tip portions 58 could also have a pyramid shape (not shown), similar to the tip of a nail.

Although the outer surfaces of the helical spikes 50 and 52 are shown as being smooth in the Figures, it is contemplated that the outer surfaces may instead be porous, pitted, or have a biocompatible coating to assist with fixation of the anchor 20 to the vertebrae 12.

It is further contemplated that the tip portions 58 of the helical spikes 50 and 52 could be covered with tip protectors (not shown) to prevent accidental sticks to surgical staff and accidental damage to tissue surrounding the vertebrae. Such tip protectors could be made of a bio-absorbable material, such as polylactic acid, or non-bio-absorbable material, such as medical grade silicon. The tip protectors would be manually removed or pushed-off during implantation of the anchor 20.

To implant the anchor 20, a tool (not shown) is used to punch two holes (not shown) in the cortical bone (not shown) of the vertebrae 12. The holes are punched in locations that correspond to the spacing of the tip portions 58 of the helical spikes 50 and 52 on the anchor 20. It should be noted that one or both of the configurations of the tip portions 58 illustrated in FIGS. 1–7 may be able to punch through the cortical bone upon rotation of the anchor 20, thus eliminating the need for the aforementioned tool to punch holes in the cortical bone.

The tip portions 58 are then placed in the holes in the vertebrae 12 and a rotatable driver (not shown) is inserted into the slot 32 in the platform 24. The driver is then rotated, causing the anchor 20 to rotate as well. It is contemplated that a cylindrical sleeve (not shown) may be placed around the intermediate portions 56 and the connecting portions 54 of the helical spikes 50 and 52 to prevent the helical spikes from deforming radially outward during the initial rotation of the anchor 20.

Rotation of the anchor 20 screws the helical spikes 50 and 52 into the cancellous bone of the vertebrae 12. The tangentially-oriented connection between the connecting portions 54 of the helical spikes 50 and 52 and the platform 24 minimizes bending loads on the connecting portions during rotation of the anchor 20. Further, the tangentially-oriented connection ensures that the force vector resulting from torque and axial force applied by the driver to platform 24 is transmitted along the helical centerline (not shown) of each of the helical spikes 50 and 52.

As the anchor 20 is rotated, the tip portion 58 of the first helical spike 50 penetrates the cancellous bone and cuts a first helical tunnel 80 (FIG. 1) through the vertebrae 12. Simultaneously, the tip portion 58 of the second helical spike 52 penetrates the cancellous bone of the vertebrae 12 and cuts a second helical tunnel 82. The first and second helical tunnels 80 and 82 are shaped like the helical spikes 50 and 52, respectively. Continued rotation of the anchor 20 embeds the helical spikes 50 and 52 deeper into the cancellous bone of the vertebrae 12. The anchor 20 is rotated until the convex end surface 38 of the platform 24 seats against the concave side surface 14 of the vertebrae 12 as shown in FIG. 1. It should be noted that in the event that the anchor 20 to be implanted is made from a polymeric or composite material, it may be necessary to use a metal anchor as a "tap" to cut the helical tunnels 80 and 82 in the vertebrae 12 prior to implantation of the polymeric or composite anchor.

Because the helical spikes 50 and 52 of the anchor 20 displace much less of the cancellous bone of the vertebrae 12 during implantation than a conventional solid shank bone screw, much less torque is required to implant the anchor in the vertebrae than is required by a conventional bone screw. Further, because the helical spikes 50 and 52 displace only a small amount of bone, the helical spikes do not create a core defect that could lead to bone deformation.

Figure 2:
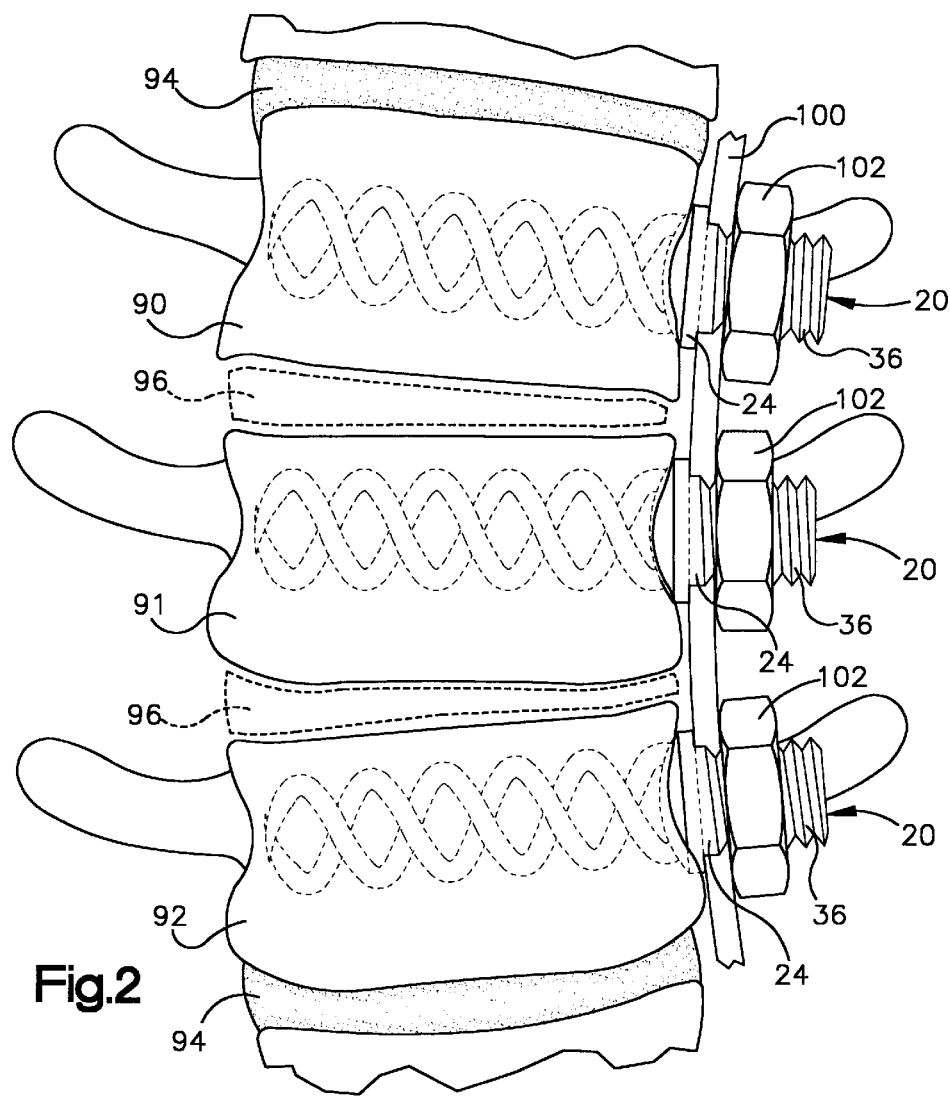
FIG. 2 is a schematic anterior view of several vertebral bodies implanted with the apparatus of FIG. 1 and connected by a spinal fixation implant in accordance with the present invention.

FIG. 2 illustrates how the anchor 20 is used for segmental spinal fixation of lumbar vertebrae to treat a patient with scoliosis. Lumbar vertebrae L3–L5, indicated by reference numbers 90, 91, and 92, respectively, are shown in FIG. 2. Normally, disk material 94 separates each of the lumbar vertebrae 90–92. However, in order to correct the scoliosis, the surgeon removes the disk material 94 between the vertebrae 90–92. The spaces left between the vertebrae 90–92 are subsequently filled with bone graft material 96 (shown schematically in FIG. 2) that fuses the vertebrae together over time. Spinal fixation instrumentation, such as a rod or a beam 100, is used to support the vertebrae 90–92 until the vertebrae fuse together.

As shown in FIG. 2, the vertebrae 90–92 are each implanted with the anchor 20 according to the present invention as described above. The beam 100, which is bent into a desired shape by the surgeon, is placed into the slot 32 in each of the anchors 20. A nut 102 is then screwed onto the threads 34 and 36 on each of the platforms 24 and is tightened to secure the beam 100 to each of the anchors 20.

When implanted, the anchors 20 are subjected to substantial forces caused by human body movement and muscle memory. In some cases, these forces can tend to pull the known screws used in such an application out of the vertebrae 90–92 or can cause the screws to toggle in the vertebrae. However, when the helical spike 50 and 52 are embedded in the vertebrae 90–92, the two helical spikes of the anchors 20 provide the anchors with a high resistance to pull-out forces. Preliminary cadaver testing indicates that the anchor 20 is so resistant to being pulled axially from a vertebral body that the vertebral body itself is likely to fail before the anchor pulls out under high tensile load. Further, the helical spikes 50 and 52, and their tangential connection with the platform 24, provide the anchors 20 with a high resistance to toggling in the vertebrae 90–92.

FIGS. 8–12 illustrate an apparatus 210 constructed in accordance with a second embodiment of the present invention. In the second embodiment of FIGS. 8–12, reference numbers that are the same as those used in the first embodiment of FIGS. 1–6 designate parts that are the same as parts in the first embodiment.

Figure 10:
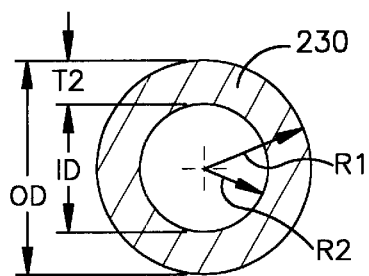
FIG. 10 is a sectional view taken along 10—10 in FIG. 8.
Figure 11:
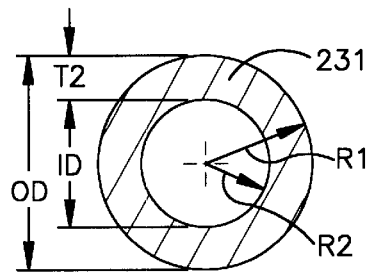
FIG. 11 is a sectional view taken along 11—11 in FIG. 8.
Figure 12:
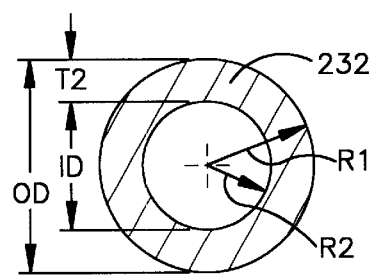
FIG. 12 is a sectional view taken along 12—12 in FIG. 8.

According to the second embodiment, the apparatus 210 comprises an anchor 220 having three helical spikes 230, 231, and 232 projecting tangentially from the end surface 38 of the platform 24. The spikes 230–232 extend around the axis 22. As shown in FIGS. 10–12, each of the helical spikes 230–232 has a tubular cross-section defined by an outer diameter OD and an inner diameter ID. The outer diameter OD of each of the helical spikes 230–232 has a first radius R1 and the inner diameter ID of each of the helical spikes has a second radius R2 that is less than the first radius R1.

Figure 8:
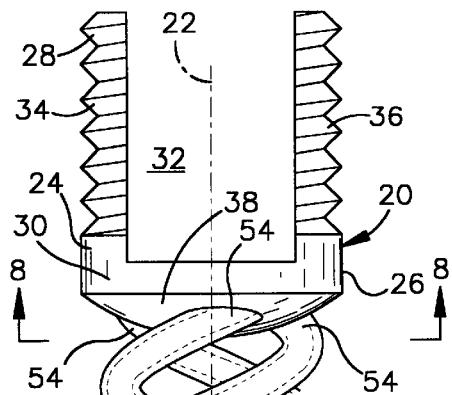
FIG. 8 is a side view illustrating a second embodiment of an apparatus in accordance with the present invention.
Figure 9:
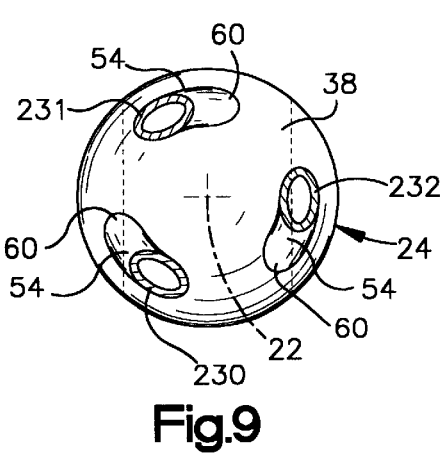
FIG. 9 is a sectional view taken along line 9—9 in FIG. 8.

As shown in FIG. 9, the connecting portions 54 at the proximal ends 60 of the helical spikes 230–232 are spaced 120° apart about the axis 22, which balances the anchor 220 and evenly distributes loads on the helical spikes. As in the first embodiment of FIGS. 1–6, in the second embodiment of FIGS. 8–12, the outer diameter of the connecting portions 54 of the helical spikes 230–232 is greater than or equal to the outer diameter of the intermediate portions 56 and the tip portions 58 of the helical spikes.

Each of the three helical spikes 230–232 extends in a helical pattern about the axis 22 at the same, constant radius R3 (FIG. 8). It is contemplated, however, that one or more of the helical spikes 230–232 could extend about the axis 22 at different radiuses. Further, it is contemplated that the radius of one or more helical spikes 230–232 could increase or decrease as the helical spikes extend away from the platform 24.

As shown in FIG. 8, the three helical spikes 230–232 have the same axial length and also have the same tubular cross-sectional shape. It is contemplated, however, that one or more of the helical spikes 230–232 could have different axial lengths. Further, it is contemplated that one or more of the helical spikes 230–232 could have a different cross-sectional shape, such as an oval shape. It also contemplated that the one or more of the helical spikes 230–232 could have different outer diameters (i.e., one spike being thicker or thinner than the other spike(s)). Finally, it is contemplated that the helical spikes 230–232 should have the same pitch, and that the pitch of the helical spikes would be selected based on the specific surgical application and quality of the bone in which the anchor 20 is to be implanted.

As in the first embodiment of FIGS. 1–6, the intermediate portion 56 of each of the helical spikes 230–232 has a second wall thickness T2 (FIGS. 10–12), defined between the first radius R1 and the second radius R2, that is less than or equal to the first wall thickness T1 (FIG. 8) of the connecting portions 54. If the first wall thickness T1 is greater than the second wall thickness T2, the additional wall thickness in the connecting portions 54 of the helical spikes 230–232 helps to increase the tensile strength of the anchor 220.

It is contemplated that the tip portions 58 of the helical spikes 230–232 will have a wall thickness (not numbered) that is greater than or equal to the wall thickness T2 of the intermediate portions 56. Additional wall thicknesses in the tip portions 58 will provide additional strength that may be beneficial during the initial stages of implantation of the anchor 220.

The wall thicknesses T1 and T2 of each of the helical spikes 230–232 may be varied, and selected, depending on the specific application for the anchor 220. By varying the wall thickness, the wall thickness can be selected to match the modulus of elasticity of the bone, which can improve fixation strength and load-sharing characteristics of the anchor 220 and the bone.

It is contemplated that the modified configurations of the helical spikes 50 and 52 illustrated in FIGS. 30–33 could also be applied to the second embodiment of FIGS. 8–12. Specifically, the connecting portions 54 and/or the tip portions 58 of the helical spikes 230–232 could have a solid cross-section, while the intermediate portions 56 have a tubular cross-section. Such modified configurations of the anchor 220 provide additional means for matching the modulus of elasticity of the bone and allow the surgeon to select a particular configuration based on the specific signal application and quality of the bone in which the anchor is to be implanted.

The tip portion 58 of each of the helical spikes 230–232 illustrated in FIG. 8 has an elongated conical shape for penetrating into a vertebrae as the platform 24 of the anchor 220 is rotated in the clockwise direction. It should be understood that the tip portions 58 of the helical spikes 230–232 of the anchor 220 could alternatively be configured like the tip portions illustrated in FIG. 7.

Although the outer surfaces of the helical spikes 230–232 are shown as being smooth in FIGS. 8–12, it is contemplated that the outer surfaces may instead be porous, pitted, or have a biocompatible coating to assist with fixation of the anchor 220 to the vertebrae.

It is further contemplated that the tip portions 58 of the helical spikes 230–232 could be covered with tip protectors (not shown) to prevent accidental sticks to surgical staff and accidental damage to tissue surrounding the vertebrae. Such tip protectors could be made of a bio-absorbable material, such as polylactic acid or a non-bio-absorbable material, such as medical grade silicon. The tip protectors would be manually removed or pushed-off during implantation of the anchor 220.

The anchor 220 according to the second embodiment of FIGS. 8–12 is implanted in a vertebrae in the same manner as the anchor 20 according to the first embodiment. Further, the anchor 220 according to the second embodiment may also be used to mount spinal fixation instrumentation in same manner as the anchor 20 according to the first embodiment.

Because the helical spikes 230–232 of the anchor 220 displace less cancellous bone during implantation than a conventional solid shank bone screw, less torque is required to implant the anchor in a vertebrae than is required by a conventional bone screw. Further, because the helical spikes displace only a small amount of bone, the helical spikes do not create a core defect that could lead to bone destruction. Finally, the anchor 220 according to the second embodiment, when implanted in a vertebrae, is highly resistant to being pulled out of the vertebrae and to toggling in the vertebrae despite being subjected to substantial forces caused by human body movement and muscle memory.

FIGS. 13–16 illustrate an apparatus 410 constructed in accordance with a third embodiment of the present invention. In the third embodiment of FIGS. 13–16, reference numbers that are the same as those used in the first embodiment of FIGS. 1–6 designate parts that are the same as parts in the first embodiment.

According to the third embodiment, the apparatus 410 comprises an identical pair of anchors 420 extending around a longitudinal axis 422. Each of the anchors 420 includes a platform 424 that is substantially wider than the platform 24 of the anchor 20 in the first embodiment of FIGS. 1–6. The platform 424 has a cylindrical outer surface 426 that extends between oppositely disposed first and second end surfaces 428 and 430. An attachment tab 440 projects axially away from the first end surface 428 of the platform 424. The attachment tab 440 includes a pair of oppositely disposed planar surfaces 442 and a pair of oppositely disposed arcuate surfaces 444.

The attachment tabs 440 provide structure for connecting spinal fixation instrumentation to each of the platforms 424 and for driving the anchors 420. The second end surface 430 of the platform 424 of each anchor 420 has a shape that is complimentary to the shape of an upper or lower surface of a vertebrae. The second end surface 430 of the platform 424 may be porous, pitted, or have a biocompatible surface coating to assist with fixation of the anchors 420 to the vertebrae.

Similar to the first embodiment of FIGS. 1–6, the anchors 420 have first and second helical spikes 450 and 452 that project from the second end surface 430 of the platform 424. The helical spikes 450 and 452 extend along the axis 422, but are significantly larger in diameter than the helical spikes 50 and 52 in the first embodiment of FIGS. 1–6. It should be understood that the anchors 420 could alternatively have three helical spikes as shown in the second embodiment of FIGS. 8–12.

Although the outer surfaces of the helical spikes 450 and 452 are shown as being smooth in FIGS. 13–16, it is contemplated that the outer surfaces may instead be porous, pitted, or have a biocompatible coating to assist with fixation of the anchors 420 to the vertebrae. It is further contemplated that the tip portions of the helical spikes 450 and 452 could be covered with tip protectors (not shown) to prevent accidental sticks to surgical staff and accidental damage to tissue surrounding the vertebrae. Such tip protectors could be made of a bio-absorbable material, such as polylactic acid, or a non-bio-absorbable material, such as medical grade silicon. The tip protectors would be manually removed or pushed-off during implantation of the anchors 420.

As shown in FIGS. 15 and 16, each of the helical spikes 450 and 452 has a tubular cross-section defined by an outer diameter OD and an inner diameter ID. The outer diameter OD of each of the helical spikes 450 and 452 has a first radius R1 and the inner diameter ID of each of the helical spikes has a second radius R2 that is less than the first radius R1.

The intermediate portion of each of the helical spikes 450 and 452 has a second wall thickness T2 (FIGS. 15 and 16) defined between the first radius R1 and the second radius R2. The second wall thickness T2 of the intermediate portion is less than or equal to a first wall thickness T1 (FIG. 13) of the connecting portion of each of the helical spikes 450 and 452. If the first wall thickness T1 is greater than the second wall thickness T2, the additional wall thickness in the connecting portions of the helical spikes 450 and 452 will help to increase the tensile strength of the anchors 420.

It is contemplated that the tip portions of the helical spikes 450 and 452 will have a wall thickness (not numbered) that is greater than or equal to the wall thickness T2 of the intermediate portions. Additional wall thickness in the tip portions will provide additional strength that may be beneficial during the initial stages of implantation of the anchors 420.

The wall thicknesses T1 and T2 of each of the helical spikes 450 and 452 may be varied, and selected, depending on the specific application for the anchors 420. By varying the wall thickness, the wall thickness can be selected to match the modulus of elasticity of the bone, which can improve fixation strength and load-sharing characteristics of the anchor 420 and the bone.

It is contemplated that the modified configurations of the helical spikes 50 and 52 illustrated in FIGS. 30–33 could also be applied to the third embodiment of FIGS. 13–16. Specifically, the connecting portions and/or the tip portions of the helical spikes 450 and 452 could have a solid cross-section, while the intermediate portions have a tubular cross-section. Such modified configurations of the anchors 420 provide additional means for matching the modulus of elasticity of the bone and allow the surgeon to select a particular configuration based on the specific surgical application and quality of the bone in which the anchor is to be implanted.

The apparatus 410 according to the third embodiment of FIGS. 13–16 is particularly useful for a corpectomy application in which a damaged vertebrae is removed. As is shown in FIG. 13, after a portion of a damaged vertebrae 460 is removed, a first one of the pair of anchors 420 is implanted into a vertebrae 462 directly above the removed vertebrae 460 and a second one of the pair of anchors 420 is implanted into a vertebrae 464 directly below the removed vertebrae.

The anchors 420 are implanted in the vertebrae 462 and 464 in much the same manner as the anchor 20 according to the first embodiment. A rotatable tool (not shown) engages the planar surfaces 442 on the attachment tab 440 and rotates each of the anchors 420 to screw the helical spikes 450 and 452 of each of the anchors into the respective vertebrae 462 and 464. The anchors 420 are implanted so that they extend co-linearly along the axis 422. When implanted, the helical spikes 450 and 452 of the anchor 420 in the vertebrae 462 extend in an upward direction from the platform 430 of the upper (as viewed in FIGS. 13 and 14) anchor, while the helical spikes 450 and 452 of the other anchor in the vertebrae 464 extend in a downward direction from the platform 430 of the lower (as viewed in FIGS. 13 and 14) anchor.

A spinal fixation implant in the form of a cylinder member 480 connects the pair of anchors 420 to structurally support the vertebral column in the absence of the removed vertebrae 460. The cylinder member 480 has a cylindrical outer surface 482 and an eccentric inner surface 484. The cylinder member 480 has a first slot 486 at a first end 488 and a second slot 490 at a second end 492. The first and second slots 486 and 490 receive the attachment tabs 440 on the anchors 420 and allow the cylinder member 480 to be inserted between the anchors. Once inserted between the anchors 420, the cylinder member 480 is then rotated relative to the anchors about the axis 422. Rotation of the cylinder member 480 brings the arcuate surfaces 444 on the attachment tabs 440 of the anchors 420 into frictional engagement with the eccentric inner surface 484 of the cylinder member, thereby securing the cylinder member.

As with the previous embodiments, the anchors 420 according to the third embodiment, when implanted, are highly resistant to being pulled out of the vertebrae 462 and 464 and to toggling in the vertebrae despite being subjected to substantial forces caused by human body movement and muscle memory. Further, because the helical spikes 450 and 452 of the anchors 420 displace relatively little of the cancellous bone of the vertebrae during implantation, a relatively small amount of torque is required to implant the anchors in the vertebrae. Further, because the helical spikes 450 and 452 displace only a small amount of bone, the helical spikes do not create a core defect that could lead to bone destruction.

FIGS. 17–22 illustrate an apparatus 510 constructed in accordance with a fourth embodiment of the present invention. The fourth embodiment of the present invention is particularly directed to an apparatus for attaching and stabilizing adjacent vertebral bodies while the vertebral bodies fuse together. As representative of the fourth embodiment, FIG. 17 illustrates the apparatus 510 implanted into an adjacent pair of lumbar vertebrae 512 and 514 in a vertebral column (not shown). It should be understood that the apparatus 510 could be implanted into any adjacent pair of vertebrae. The vertebrae 512 has a side surface 516 and a lower surface (or end plate) 517 (FIG. 18). The vertebrae 514 has a side surface 518 and an upper surface (or end plate) 519.

The apparatus 510 comprises an interbody stabilizer 520 made from a biocompatible material, such as titanium or stainless steel. It is contemplated that the biocompatible material used for the interbody stabilizer 520 could be polymeric or composite (i.e., carbon fiber or other biologic composite) in nature. It is further contemplated that the biocompatible material used to make the interbody stabilizer 520 could also be biodegradable.

The interbody stabilizer 520 is centered about a longitudinal axis 522 (FIG. 19). The interbody stabilizer 520 includes a platform 524 having a generally cylindrical outer surface 526 extending between oppositely disposed first and second ends 528 and 530. The second end 530 of the platform 524 includes an end surface 538 that extends transverse to the side surfaces 516 and 518 of the adjacent vertebrae 512 and 514, respectively. The end surface 538 of the platform 524 has a shape that is complimentary to the side surfaces 516 and 518 of the vertebrae 512 and 514, respectively. The end surfaces 538 of the platform 524 may be porous, pitted, or have a biocompatible surface coating to assist with fixation of the interbody stabilizer to the vertebrae 512 and 514.

The platform 524 of the interbody stabilizer 520 further includes an axial passage 540 that extends from the first end 528 to the end surface 538. The passage 540 has a hexagonal configuration for receiving a rotatable driver (not shown).

First and second helical spikes 550 and 552 project from the end surface 538 of the platform 524. The helical spikes 550 and 552 resemble a pair of inter-twined corkscrews. As shown in FIGS. 21 and 22, each of the helical spikes 550 and 552 has a tubular cross-section defined by an outer diameter OD and an inner diameter ID. The outer diameter OD of each of the helical spikes 550 and 552 has a first radius R1 and the inner diameter ID of each of the helical spikes has a second radius R2 that is less than the first radius R1.

According to the fourth embodiment illustrated in FIGS. 17–22, the first and second helical spikes 550 and 552 extend around the axis 522. The spikes 550 and 552 extend in a helical pattern about the axis 522 at the same, constant radius R1. It is contemplated, however, that the first and second helical spikes 550 and 552 could extend about the axis 522 at different radiuses. Further, it is contemplated that the radius of one or both of the first and second helical spikes 550 and 552 could increase or decrease as the helical spikes extend away from the platform 524. In order for the interbody stabilizer 520 to be implanted endoscopically through a typical cannula (not shown), it is preferred that the platform 524 and the helical spikes 550 and 552 are less than 20 mm in overall diameter. It should be understood that the interbody stabilizer 520 could have an overall diameter that is greater than 20 mm for certain applications, and that the interbody stabilizer could also be implanted in an open surgical procedure.

In the fourth embodiment of FIGS. 17–22, the first and second helical spikes 550 and 552 have the same axial length, and also have the same tubular cross-sectional shape. It is contemplated, however, that the first and second helical spikes 550 and 552 could have different axial lengths. Further, it is contemplated that the helical spikes 550 and 552 could have a different cross-sectional shape, such as an oval shape. It also contemplated that the first and second helical spikes 550 and 552 could have different outer diameters (i.e., one spike being thicker than the other spike). Finally, it is contemplated that the helical spikes 550 and 552 should have the same pitch, and that the pitch of the helical spikes would be selected based on the specific surgical application and quality of the bone in which the interbody stabilizer 520 is to be implanted.

Each of the first and second helical spikes 550 and 552 can be divided into three portions: a connecting portion 554, an intermediate portion 556, and a tip portion 558. The connecting portion 554 of each of the helical spikes 550 and 552 is located at a proximal end 560 that adjoins the end surface 538 of the platform 524. The connecting portion 554 may include barbs (not shown) for resisting pull-out of the helical spikes 550 and 552 from the vertebrae 512 and 514. According to one method for manufacturing the interbody stabilizer 520, the connecting portion 554 of each of the helical spikes 550 and 552 is fixedly attached to the platform 524 by inserting, in a tangential direction, the proximal ends 560 of the helical spikes into openings (not shown) in the end surfaces 38 and welding the connecting portions 554 to the platform. The inserted proximal ends 560 of the helical spikes 550 and 552 help to reduce tensile bending stresses on the helical spikes under a tensile load.

Alternatively, the helical spikes 550 and 552 may be formed integrally with the platform 524, such as by casting the interbody stabilizer 520. If the interbody stabilizer 520 is cast, it is contemplated that a fillet (not shown) may be added at the junction of the helical spikes 550 and 552 and the platform 524 to strengthen the junction and minimize stress concentrations at the connecting portions 554. The fillet at the junction of the helical spikes 550 and 552 and the platform 524 also helps to reduce bending stresses in the connecting portions 554 of the helical spikes under a tensile load.

As best seen in FIG. 20, the connecting portions 554 at the proximal ends 560 of the first and second helical spikes 550 and 552 are spaced 180° apart about the axis 522 to balance the interbody stabilizer 520 and evenly distribute loads on the helical spikes. The connecting portion 554 of each of the helical spikes 550 and 552 has a first wall thickness T1 (FIG. 19) defined between the first radius R1 and the second radius R2.

The tip portion 558 of each of the helical spikes 550 and 552 is located at a distal end 562 of the helical spikes. The intermediate portion 556 of each of the helical spikes 550 and 552 extends between the tip portion 558 and the connecting portion 554. The intermediate portion 556 and the tip portion 558 of each of the helical spikes 550 and 552 have an outer diameter that is less than or equal to the outer diameter of the connecting portions 554. If the outer diameter of the intermediate portions 556 and the tip portions 558 is less than the outer diameter of the connecting portions 554, the increased thickness of the connecting portions 554 of the helical spikes 550 and 552 will help to provide the interbody stabilizer 520 with increased tensile strength at the junction of the helical spikes and the platform 524.

The intermediate portion 556 of each of the helical spikes 550 and 552 has a second wall thickness T2 (FIGS. 21, 22) defined between the first radius R1 and the second radius R2. The second wall thickness T2 of the intermediate portion 556 is less than or equal to the first wall thickness T1 of the connection portion 554. If the first wall thickness T1 is greater than the second wall thickness T2, the additional wall thickness in the connecting portions 554 of the helical spikes 550 and 552 will help to increase the tensile strength of the interbody stabilizer 520.

It is contemplated that the tip portions 558 of the helical spikes 550 and 552 will have a wall thickness (not numbered) that is greater than or equal to the wall thickness T2 of the intermediate portions 556. Additional wall thickness in the tip portions 558 will provide additional strength that may be beneficial during the initial stages of implantation of the interbody stabilizer 520.

It is further contemplated that the wall thicknesses T1 and T2 of each of the helical spikes 550 and 552 may be varied and selected, depending on the specific application for the interbody stabilizer 520. By varying the wall thickness, the wall thickness can be selected to match the modulus of elasticity of the bone, which can improve fixation strength and load-sharing characteristics of the interbody stabilizer 520 and the bone.

It is contemplated that the modified configurations of the helical spikes 50 and 52 illustrated in FIGS. 30–33 could also be applied to the third embodiment of FIGS. 17–22. Specifically, the connecting portions and/or the tip portions of the helical spikes 550 and 552 could have a solid cross-section, while the intermediate portions 556 have a tubular cross-section. Such modified configurations of the interbody stabilizer 520 provide additional means for matching the modulus of elasticity of the bone and allow the surgeon to select a particular configuration based on the specific surgical application and quality of the bone in which the interbody stabilizer is to be implanted.

The tip portion 558 of each of the helical spikes 550 and 552 is self-penetrating and provides the helical spikes with the ability to penetrate into a respective one of the vertebrae 512 and 514 as the platform 524 of the interbody stabilizer 520 is rotated in a clockwise direction. The tip portions 558 illustrated in FIGS. 17–22 have an elongated conical shape with a sharp pointed tip 568. FIG. 23 illustrates an alternative, self-tapping configuration for the tip portions 558 which includes a planar surface 566 for driving into the vertebrae 512 and 514, in the same manner that a wood chisel turned upside-down drives into wood, as the platform 524 is rotated. It is contemplated that the tip portions 558 could also have a pyramid shape, similar to the tip of a nail.

Although the outer surfaces of the helical spikes 550 and 552 are shown as being smooth in FIGS. 17–22, it is contemplated that the outer surfaces may instead be porous, pitted, or have a biocompatible coating to assist with fixation of the interbody stabilizer 520 to the vertebrae 512 and 514.

It is further contemplated that the tip portions 558 of the helical spikes 550 and 552 could be covered with tip protectors (not shown) to prevent accidental sticks to surgical staff and accidental damage to tissue surrounding the vertebrae. Such tip protectors could be made of a bioabsorbable material, such as polylactic acid, or a non-bioabsorbable material, such as medical grade silicon. The tip protectors would be manually removed or pushed-off during implantation of the interbody stabilizer 520.

FIGS. 17 and 18 illustrate the interbody stabilizer 520 implanted in the adjacent lumbar vertebrae 512 and 514 to stabilize the vertebrae. First, disk material that normally separates the vertebrae 512 and 514 is removed by the surgeon. Removal of the disk material leaves an interbody space 560 (FIG. 18) between the vertebrae 512 and 514. A tool (not shown) is then used to punch a hole (not shown) in the cortical bone (not shown) of each of the vertebrae 512 and 514. The hole in the vertebrae 512 may be punched in either the side surface 516 or the lower surface 517. The hole in the vertebrae 514 may be punched in either the side surface 518 or the upper surface 519. The holes in the vertebrae 512 and 514 are punched in locations that correspond to the spacing of the tip portions 558 of the helical spikes 550 and 552 of the interbody stabilizer 520. The holes in the vertebrae 512 and 514 are intended to make the initial rotation of the stabilizer 520 easier. It should be noted that one or both of the configurations of the tip portions 558 illustrated in FIGS. 17–23 may be able to punch through the cortical bone upon rotation of the interbody stabilizer 520, thus eliminating the need for the aforementioned tool to punch holes in the cortical bone.

The tip portions 558 of the interbody stabilizer 520 are placed in the holes in the vertebrae 512 and 514 and a rotatable driver (not shown) is inserted into the passage 540 in the platform 524. The driver is then rotated, causing the interbody stabilizer 520 to rotate as well. It is contemplated that a cylindrical sleeve (not shown) may be placed around the intermediate portions 556 and the connecting portions 554 of the helical spikes 550 and 552 to prevent the helical spikes from deforming radially outward during the initial rotation of the interbody stabilizer 520.

Rotation of the interbody stabilizer 520 screws the helical spikes 550 and 552 into the vertebrae 512 and 514, respectively. The tangentially-oriented connection between the connection portions 554 of the helical spikes 550 and 552 and the platform 524 minimizes bending loads on the connecting portions during rotation of the interbody stabilizer 520. Further, the tangentially-oriented connection ensures that the force vector resulting from axial force torque and applied by the driver to the platform 524 is transmitted along the helical centerline (not shown) of each of the helical spikes 550 and 552.

As the interbody stabilizer 520 is rotated, the tip portion 558 of the first helical spike 550 penetrates the cancellous bone in the vertebrae 512 and cuts a first helical segment 582 of a first tunnel 580 (FIG. 17) in the vertebrae 512. Simultaneously, the tip portion 558 of the second helical spike 552 penetrates the cancellous bone of the vertebrae 514 and cuts a first helical segment 602 of a second tunnel 600 in the vertebrae 514.

At some point between 90° and 180° of rotation of the interbody stabilizer 520, the tip portions 558 of the helical spikes 550 and 552 penetrate back out of the vertebrae 512 and 514, respectively and into the interbody space 560. More specifically, the tip portion 558 of the first helical spike 550 projects through the lower surface 517 of the vertebrae 512 and into the interbody space 560. Simultaneously, the tip portion 558 of the second helical spike 552 projects through the upper surface 519 of the vertebrae 514 and into the interbody space 560.

As the interbody stabilizer 520 is rotated beyond 180°, the tip portions 558 of the helical spikes 550 and 552 move through the interbody space 560 and engage the vertebrae 514 and 512, respectively. The tip portion 558 of the first helical spike 550 penetrates into the upper surface 519 of the vertebrae 514, while the tip portion 558 of the second helical spike 552 projects through the lower surface 517 of the vertebrae 512. Continued rotation of the interbody stabilizer 520 causes the tip portion 558 of the first helical spike 550 to cut a second helical segment 584 of the first tunnel 580 in the vertebrae 514. Similarly, the continued rotation causes the tip portion 558 of the second helical spike 552 to cut a second helical segment 604 of the second tunnel 600 in the vertebrae 512.

After another 90° to 180° of rotation of the interbody stabilizer 520, the tip portions 558 of the helical spikes 550 and 552 penetrate back out of the vertebrae 514 and 512, respectively, and into the interbody space 560. More specifically, the tip portion 558 of the first helical spike 550 projects through the upper surface 519 of the vertebrae 514 and the tip portion 558 of the second helical spike 552 projects through the lower surface 517 of the vertebrae 512.

As the interbody stabilizer 520 is rotated further, the tip portions 558 of the helical spikes 550 and 552 move through the interbody space 560 and re-engage the vertebrae 512 and 514, respectively. The tip portion 558 of the first helical spike 550 penetrates the lower surface 517 of the vertebrae 512 and cuts a third helical segment 586 of the first tunnel 580 in the vertebrae 512. Simultaneously, the tip portion 558 of the second helical spike 552 penetrates the lower surface 519 of the vertebrae 514 and cuts a third helical segment 606 of the second tunnel 600 in the vertebrae 514.

After further rotation of the interbody stabilizer 520, the tip portions 558 of the helical spikes 550 and 552 again penetrate back out of the vertebrae 512 and 514, respectively and into the interbody space 560. The tip portion 558 of the first helical spike 550 projects through the lower surface 517 of the vertebrae 512, while the tip portion 558 of the second helical spike 552 projects through the upper surface 519 of the vertebrae 514. The interbody stabilizer 520 is then rotated so that the tip portions 558 of the helical spikes 550 and 552 move through the interbody space 560 and re-engage the vertebrae 514 and 512, respectively. The tip portion 558 of the first helical spike 550 again penetrates into the upper surface 519 of the vertebrae 514, causing the tip portion 558 of the first helical spike 550 to cut a fourth helical segment 588 of the first tunnel 580 in the vertebrae 514. Similarly, the tip portion 558 of the second helical spike 552 again penetrates through the lower surface 517 of the vertebrae 512, causing the tip portion 558 of the second helical spike 552 to cut a fourth helical segment 608 of the second tunnel 600 in the vertebrae 512.

This pattern of screwing the helical spikes 550 and 552 of the interbody stabilizer 520 into and out of each of the vertebrae 512 and 514 in an alternating manner continues with each revolution of the platform 524 by the driver. The continued rotation of the platform 524 embeds the helical spikes 550 and 552 of the interbody stabilizer 520 into the vertebrae 512 and 514 and attaches the interbody stabilizer to each of the vertebrae. With each rotation of the interbody stabilizer 520, the connection between the interbody stabilizer and each of the vertebrae 512 and 514 gets stronger. The attachment of the interbody stabilizer 520 to each of the vertebrae 512 and 514 thus fastens, or pins, the vertebrae together, yet spaced apart. Rotation of the platform 524 is terminated when the end surface 538 of the platform seats against one or both of the side surfaces 516 and 518 of the vertebrae 512 and 514, respectively. It should be noted that in the event that the interbody stabilizer 520 to be implanted is made from a polymeric or composite material, it may be necessary to use a metal interbody stabilizer as a "tap" to cut the helical tunnels 580 and 680 in the vertebrae 512 and 514, respectively, prior to implantation of the polymeric or composite interbody stabilizer.

Once the interbody stabilizer 520 is implanted, bone graft material 590 (shown schematically in FIGS. 17 and 18) for permanently fusing the vertebrae 512 and 514 is placed into the interbody space 560. More specifically, the bone graft material 590 is placed into a cavity 592 defined by the helical spikes 550 and 552, the lower surface 517 of the vertebrae 512, and the lower surface 519 of the vertebrae 514. The bone graft material 590, which may comprise bone chips and/or synthetic bone material, is placed into the cavity 592 through the axial passage 540 in the platform 524 of the interbody stabilizer 520. A sufficient amount of the bone graft material 590 is placed into the cavity 592 to fill not only the cavity, but also the entire interbody space 560.

When implanted, the interbody stabilizer 520 is attached to both of the vertebrae 512 and 514 and securely fastens the vertebrae together. Because each of the helical spikes 550 and 552 penetrates into and subsequently out of each of the vertebrae 512 and 514, the helical spikes provide multiple fixation locations between the interbody stabilizer 520 and the vertebrae that pin the vertebrae together. The interbody stabilizer 520 is therefore able to resist relative movement of the vertebrae 512 and 514 toward or away from each other, and does not rely on surrounding ligaments to stabilize the vertebrae. More specifically, the interbody stabilizer 520 resists relative movement of the vertebrae 512 and 514, through bending or rotation, along any one of the three planes of motion (sagittal, coronal, or horizontal). Thus, the interbody stabilizer 520 is able to maintain proper intervertebral spacing and provide effective temporary stabilization of the adjacent vertebrae 512 and 514, despite substantial forces on the interbody stabilizer caused by human body movement and muscle memory, while the bone graft material 590 fuses the vertebrae together. Advantageously, the interbody stabilizer 520 has a simple one-piece construct that does not require a large amount of torque to implant, and does not require substantial cutting of cortical bone (i.e., a reaming or tapping procedure) to prepare the vertebrae 512 and 514 to accept the interbody stabilizer. Thus, the interbody stabilizer 520 is not only a simplified construct, but also simplifies the steps required for implantation into adjacent vertebrae.

Figure 24:
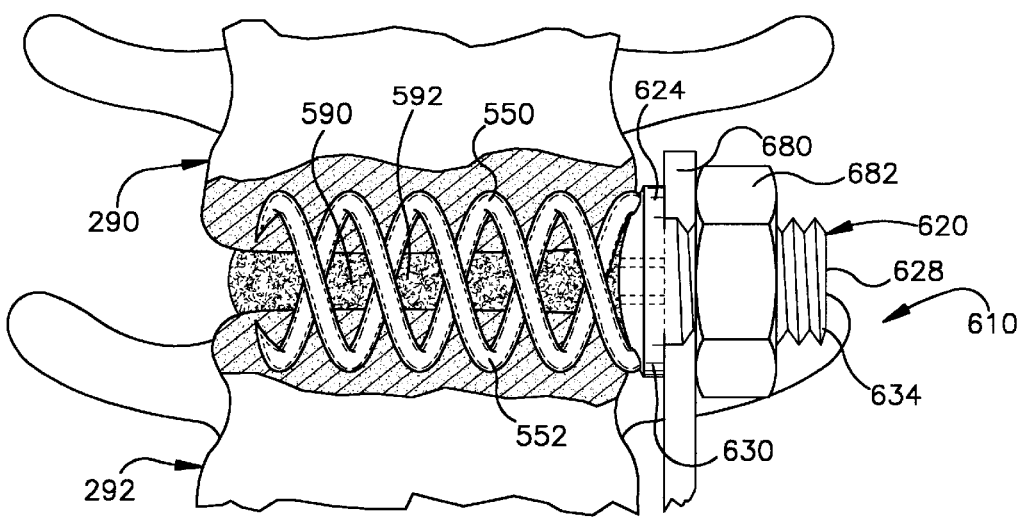
FIG. 24 is a schematic anterior view illustrating a fifth embodiment of the present invention.

FIG. 24 illustrates an apparatus 610 constructed in accordance with a fifth embodiment of the present invention. In the fifth embodiment of FIG. 24, reference numbers that are the same as those used in the fourth embodiment of FIGS. 17–22 designate parts that are the same as parts in the fourth embodiment.

According to the fifth embodiment, the apparatus 610 comprises an interbody stabilizer 620 having a platform 624. The platform 624 includes a generally rectangular slot (not numbered) that extends axially from an open end 628 of the platform toward an opposite end 630 of the platform. Adjacent the open end 628, the platform 624 includes first and second segments of external threads 634 (only one of which is shown) that are separated by the slot. The slot and the threads 634 provide structure for connecting spinal fixation instrumentation to the platform 624. The first and second helical spikes 550 and 552 project from the end surface 538 at the second end 630 of the platform 624.

FIG. 24 illustrates how the interbody stabilizer 620 may be used for segmental spinal fixation. Lumbar vertebrae L3 and L4, indicated by reference numbers 690 and 692, respectively, are shown in FIG. 24. The interbody stabilizer 620 according to the fifth embodiment of the present invention is implanted in the interbody space between the vertebrae 690 and 692. The interbody stabilizer 620 is implanted into the vertebrae 690 and 692 in much the same manner as described above regarding the first embodiment. A rotatable driver (not shown) fits into the slot in the interbody stabilizer 620 and is used to rotate the interbody stabilizer.

Once the interbody stabilizer 620 is implanted, spinal fixation instrumentation such as a beam 680 which has been bent into a desired shape by the surgeon, is placed into the slot in the interbody stabilizer. A nut 682 is then screwed onto the threads 634 on the platform 624 and tightened to secure the beam 680 to the interbody stabilizer 620. As in the first embodiment, the interbody stabilizer 620 fastens the vertebrae 690 and 692 together and stabilizes the vertebrae until the bone graft material 590 placed in the cavity 592 defined inside each of the interbody stabilizers fuses the vertebrae. The beam 680 helps to further support the vertebrae 690 and 692 until the vertebrae fuse together.

FIGS. 25–29 illustrate an apparatus 710 constructed in accordance with a sixth embodiment of the present invention. In the sixth embodiment of FIGS. 25–29, reference numbers that are the same as those used in the fourth embodiment of FIGS. 17–22 designate parts that are the same as parts in the fourth embodiment.

Figure 27:
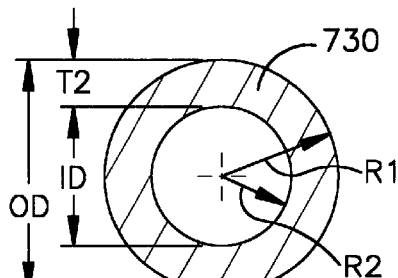
FIG. 27 is a sectional view taken along 27—27 in FIG. 25.
Figure 28:
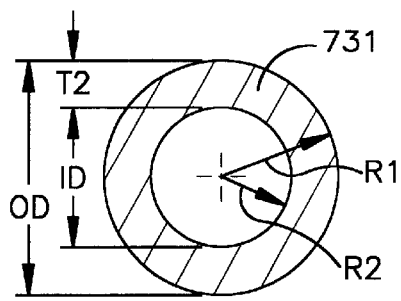
FIG. 28 is a sectional view taken along 28—28 in FIG. 25.
Figure 29:
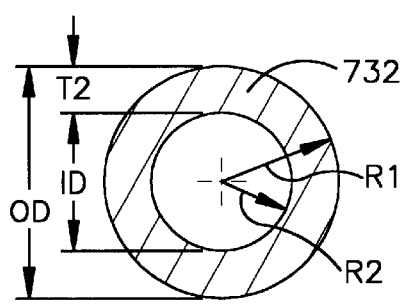
FIG. 29 is a sectional view taken along 29—29 in FIG. 25.

According to the sixth embodiment, the apparatus 710 comprises an interbody stabilizer 720 having three helical spikes 730, 731, and 732 projecting tangentially from the end surface 538 of the platform 524. The spikes 730–732 are centered about the axis 522. As shown in FIGS. 27–29, each of the helical spikes 730–732 has a tubular cross-section defined by an outer diameter OD and an inner diameter ID. The outer diameter OD of each of the helical spikes 50 and 52 has a first radius R1 and the inner diameter ID of each of the helical spikes has a second radius R2 that is less than the first radius R1.

Figure 25:
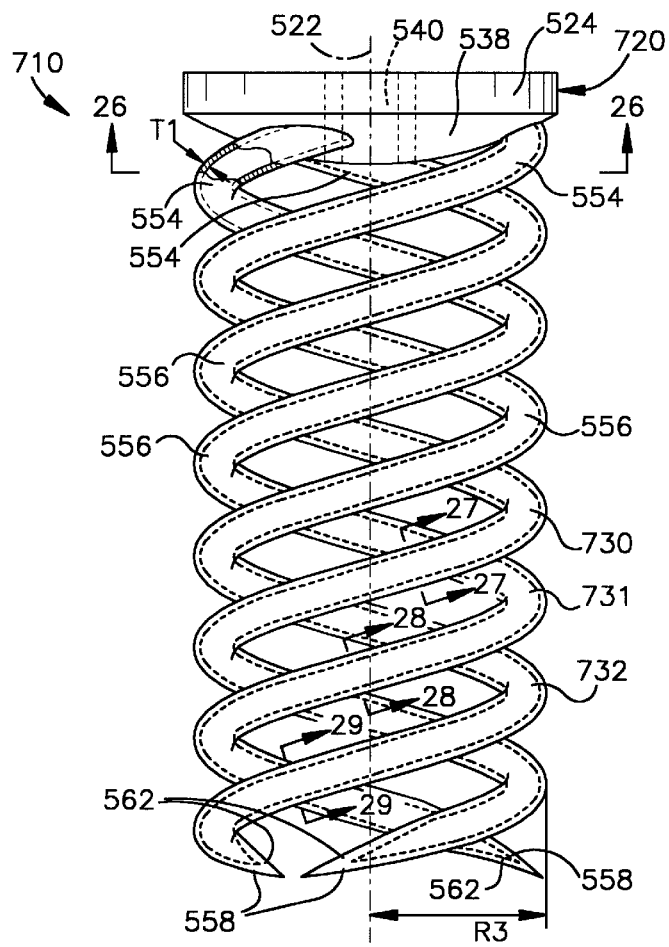
FIG. 25 is a side view illustrating a sixth embodiment of an apparatus for implanting in an adjacent pair of vertebral bodies in accordance with the present invention.
Figure 26:
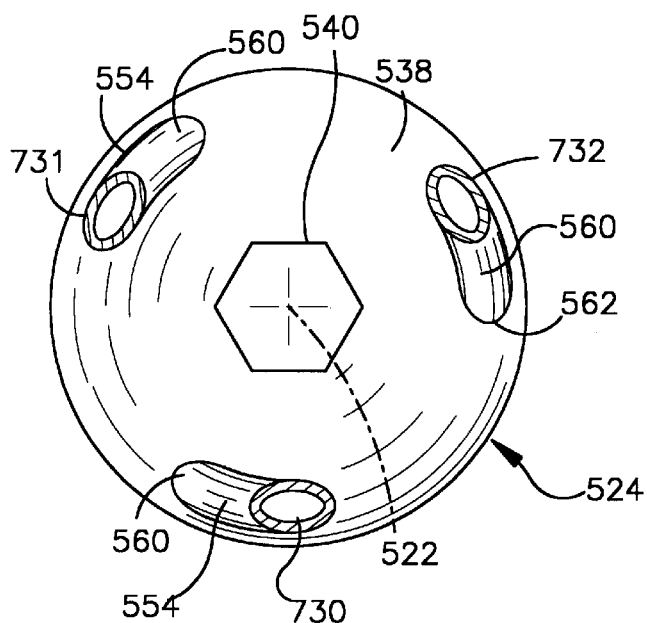
FIG. 26 is a sectional view taken along line 26—26 in FIG. 25.

As shown in FIG. 26, the connecting portions 554 at the proximal ends 560 of the helical spikes 730–732 are spaced 120° apart about the axis 522, which balances the interbody stabilizer 720 and evenly distributes loads on the helical spikes. As in the fourth embodiment of FIGS. 17–22, in the sixth embodiment of FIGS. 25–29, the outer diameter of the connecting portions 554 of the helical spikes 730–732 is greater than or equal to the outer diameter of the intermediate portions 556 and the tip portions 558 of the helical spikes.

Each of the three helical spikes 730–732 extends in a helical pattern about the axis 522 at the same, constant radius R1. It is contemplated, however, that one or more of the helical spikes 730–732 could extend about the axis 522 at different radiuses. Further, it is contemplated that the radius of one or more helical spikes 730–732 could increase or decrease as the helical spikes extend away from the platform 524.

As shown in FIG. 25, the three helical spikes 730–732 have the same axial length and also have the same tubular cross-sectional shape. It is contemplated, however, that one or more of the helical spikes 730–732 could have different axial lengths. Further, it is contemplated that one or more of the helical spikes 730–732 could have a different cross-sectional shape, such as an oval shape. It also contemplated that the one or more of the helical spikes 730–732 could have different outer diameters (i.e., one spike being thicker or thinner than the other spike(s)). Finally, it is contemplated that the helical spikes 730–732 should have the same pitch, and that the pitch of the helical spikes would be selected based on the specific surgical application and quality of the bone in which the interbody stabilizer 720 is to be implanted.

As in the fourth embodiment of FIGS. 17–22, the intermediate portion 556 of each of the helical spikes 730–732 has a second wall thickness T2 (FIGS. 27–29) defined between the first radius R1 and the second radius R2. The second wall thickness T2 of the intermediate portion 556 is less than or equal to the first wall thickness T1 (FIG. 25) of the connecting portions 554. If the first wall thickness T1 is greater than the second wall thickness T2, the additional wall thickness in the connecting portions 554 of the helical spikes 730–732 will help to increase the tensile strength of the interbody stabilizer 720.

It is further contemplated that the tip portions 558 of the helical spikes 730–732 will have a wall thickness (not numbered) that is greater than or equal to the wall thickness T2 of the intermediate portions 556. Additional wall thickness in the tip portions 558 will provide additional strength that may be beneficial during the initial stages of implantation of the interbody stabilizer 720.

It is further contemplated that the wall thicknesses T1 and T2 of each of the helical spikes 730–732 may be varied, and selected, depending on the specific application for the interbody stabilizer 720. By varying the wall thickness, the wall thickness can be selected to match the modulus of elasticity of the bone, which can improve fixation strength and load-sharing characteristics of the interbody stabilizer 720 and the bone.

It is contemplated that the modified configurations of the helical spikes 50 and 52 illustrated in FIGS. 30–33 could also be applied to the sixth embodiment of FIGS. 25–29. Specifically, the connecting portions and/or the tip portions of the helical spikes 730 and 732 could have a solid cross-section, while the intermediate portions 556 have a tubular cross-section. Such modified configurations of the interbody stabilizer 720 provide additional means for matching the modulus of elasticity of the bone and allow the surgeon to select a particular configuration based on the specific surgical application and quality of the bone in which the interbody stabilizer is to be implanted.

The tip portion 558 of each of the helical spikes 730–732 illustrated in FIG. 25 has an elongated conical shape for penetrating into a vertebrae as the platform 524 of the interbody stabilizer 720 is rotated in the clockwise direction. It should be understood that the tip portions 558 of the helical spikes 730–732 of the interbody stabilizer 720 could alternatively be configured like the tip portions illustrated in FIG. 23.

Although the outer surfaces of the helical spikes 730–732 are shown as being smooth in FIGS. 25–29, it is contemplated that the outer surfaces may instead be porous, pitted, or have a biocompatible coating to assist with fixation of the interbody stabilizer 720 to the vertebrae. It is further contemplated that the tip portions 558 of the helical spikes 730–732 could be covered with tip protectors (not shown) to prevent accidental sticks to surgical staff and accidental damage to tissue surrounding the vertebrae. Such tip protectors could be made of a bio-absorbable material, such as polylactic acid, or a non-bio-absorbable material, such as medical grade silicon. The tip protectors would be manually removed or pushed-off during implantation of the interbody stabilizer 720.

The interbody stabilizer 720 according to the sixth embodiment of FIGS. 25–29 is implanted into an adjacent pair of vertebrae in the same manner as the interbody stabilizer 720 according to the fourth embodiment. Further, the interbody stabilizer 720 according to the sixth embodiment may also be used to mount spinal fixation instrumentation as shown in the fifth embodiment of FIG. 24. When implanted, the interbody stabilizer 720 is attached to both of the adjacent vertebrae and fastens the vertebrae together. Further, the interbody stabilizer 720 maintains proper intervertebral spacing and provides effective temporary stabilization of the adjacent vertebrae while the bone graft material placed in the cavity in the interbody stabilizer fuses the vertebrae together. Advantageously, the interbody stabilizer 720 is a simple one-piece construct that does not require a large amount of torque to implant and does not require substantial cutting of cortical bone (i.e., a reaming or tapping procedure) to prepare the adjacent vertebrae to accept the interbody stabilizer.

Figure 34:
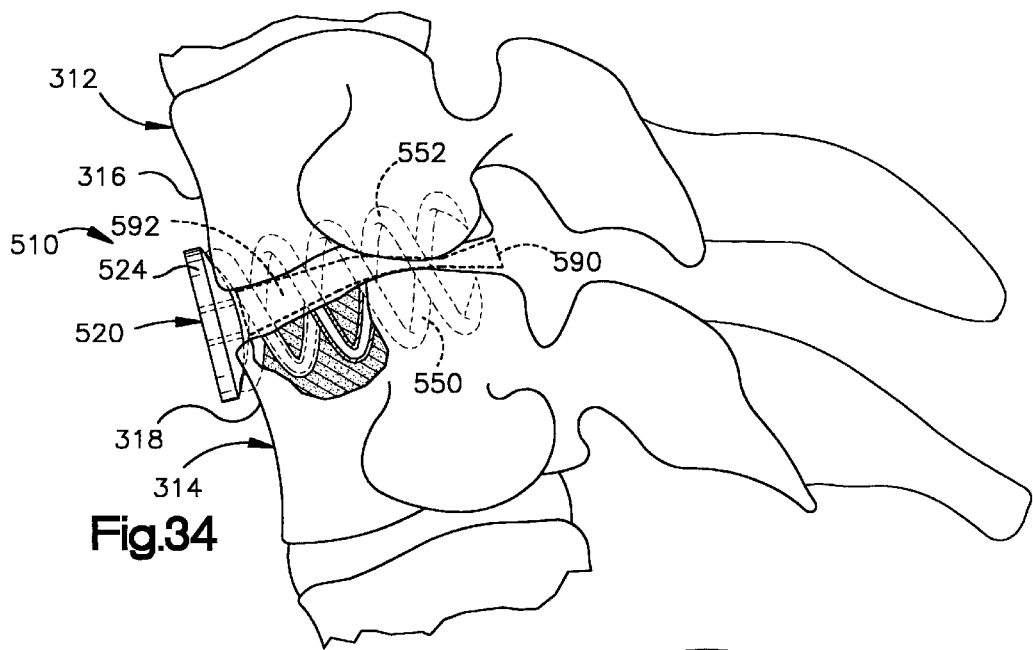
FIG. 34 is a side view illustrating a cervical application of the apparatus of FIG. 19 in accordance with the present invention.

FIG. 34 illustrates a cervical application of the apparatus 510 of FIG. 19 in accordance with the present invention. In FIG. 34, reference numbers that are the same as those used in the third embodiment of FIGS. 17–22 designate parts that are the same as parts in the third embodiment.

As shown in FIG. 34, the interbody stabilizer 520 has the first and second helical spikes 550 and 552 with tubular cross sections. The interbody stabilizer 520 is implanted into two cervical vertebrae 312 and 314 in the same manner as described above regarding the first embodiment. The end surface 538 of the interbody stabilizer 520 seats against anterior surfaces 316 and 318 of the vertebrae 312 and 314, respectively. As in the first embodiment, the interbody stabilizer 520 fastens the vertebrae 312 and 314 and stabilizes the vertebrae until the bone graft material 590 placed in the cavity 592 in the interbody stabilizer fuses the vertebrae.

It should be noted that the interbody stabilizers according to the present invention can be used not only to stabilize a degenerative disc, but can also be used to correct spinal deformity such as scoliosis, kyphosis, lordosis, and spondylosisthesis.

Figure 35:
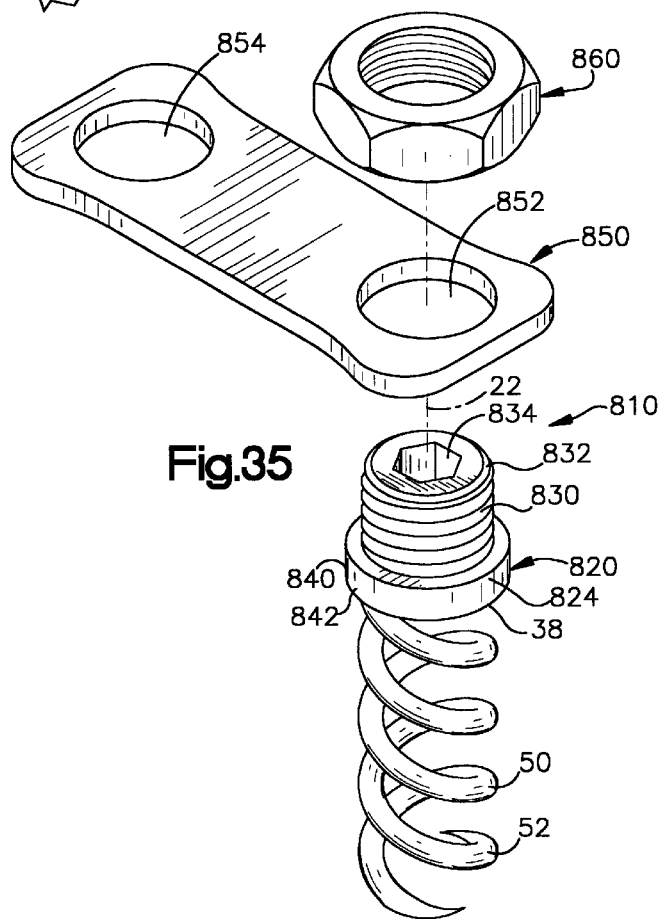
FIG. 35 is an exploded perspective view illustrating a seventh embodiment of an apparatus in accordance with the present invention.
Figure 36:
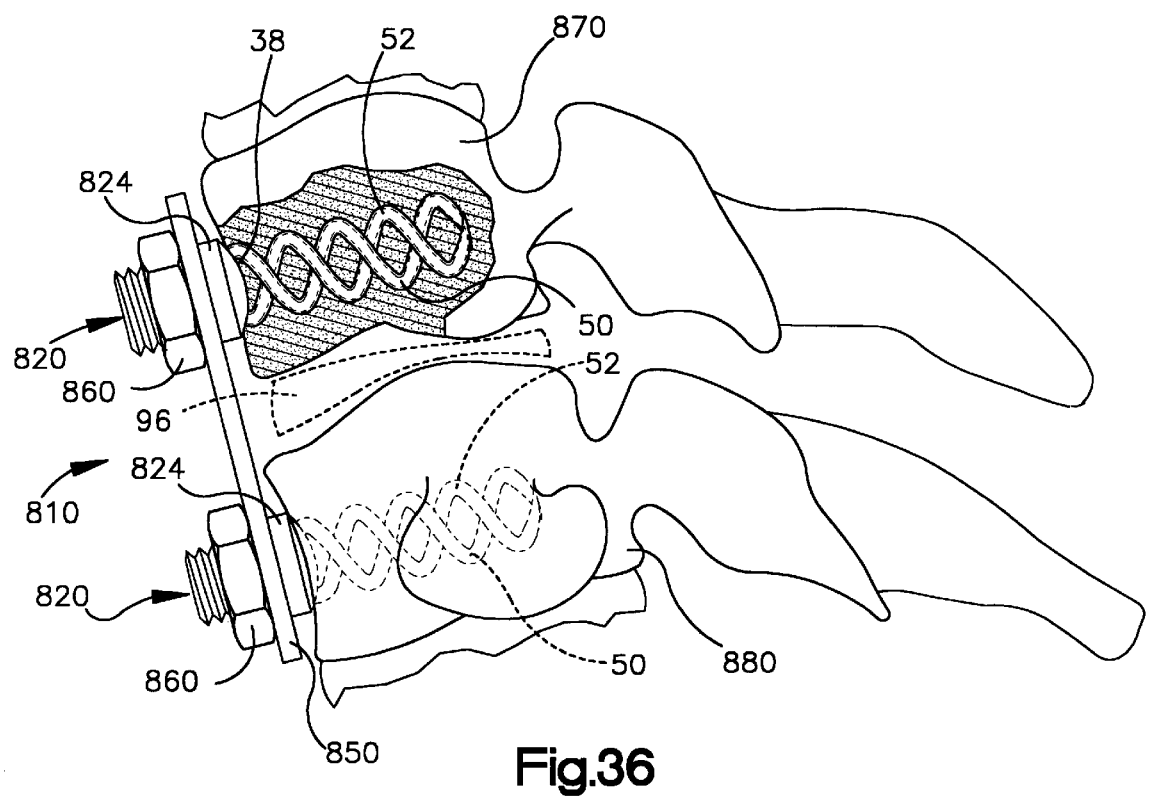
FIG. 36 is a schematic view of the apparatus of FIG. 35 implanted in a pair of cervical vertebrae.

FIGS. 35 and 36 illustrate an apparatus 810 constructed in accordance with a seventh embodiment of the present invention. In the seventh embodiment of FIGS. 35 and 36, reference numbers that are the same as those used in the first embodiment of FIGS. 1–6 designate parts that are the same as parts in the first embodiment.

According to the seventh embodiment, the apparatus 810 comprises an anchor 820 having a platform 824. The platform 824 has a threaded outer surface 830 adjacent a first end portion 832 and a cylindrical outer surface 840 adjacent a second end portion 842. The first end portion 832 of the platform 824 further includes an axial recess 834. The recess 834 has a hexagonal configuration for receiving a tool (not shown) for drivingly rotating the anchor 820. The first and second helical spikes 50 and 52 have a tubular cross-section and project from the end surface 38 of the platform 824.

The apparatus 810 further includes a plate 850 and a nut 860. The plate 850 has a first opening 852 for receiving the portion of the platform 824 which has the threaded outer surface 830. The plate 850 has a second opening 854 for receiving a second anchor 820 (see FIG. 36) or other fixation instrumentation (not shown). When the anchor 820 is implanted in a vertebrae, the nut 860 screws onto the threaded outer surface 830 of the platform 824 to secure the plate 850 to the anchor 820.

The anchor 820 according to the seventh embodiment of FIGS. 35 and 36 is implanted in a vertebrae in the same manner as the anchor 20 according to the first embodiment. FIG. 36 shows a pair of the anchors 820 implanted in two cervical vertebrae 870 and 880. The end surface 38 of each of the anchors 820 engages a respective anterior surface on each of the vertebrae 870 and 880. The plate 850 connects the anchors 820 to help support the vertebrae 870 and 880 and transfer loads between the vertebrae until bone graft material 890 fuses the vertebrae. Like the anchor 820 according to the seventh embodiment, the anchor 320 according to the third embodiment, when implanted in the vertebrae, is highly resistant to being pulled out of the vertebrae and to toggling in the vertebrae despite being subjected to substantial forces caused by human body movement and muscle memory.

From the above description of the invention, those skilled in the art will perceive improvements, changes and modifications. It should be understood that the present invention can be used for a variety of purposes and can be implanted in other bones besides bones in the vertebrae column. Further, the present invention could be used to attach and stabilize other adjacent bones, not just bones in the spine or pelvis. It is further contemplated that the present invention could comprise a single helical spike, or more than three spikes. Such improvements, changes and modifications within the skill of the art are intended to be covered by the appended claims.

Having described the invention, I claim:

1. An apparatus for implantation into a bone in a patient's spine or pelvis, said apparatus, when implanted, being resistant to toggling in the bone and to being pulled from the bone, said apparatus comprising:

a platform having a first surface for facing a bone in a patient's spine or pelvis, said first surface being solid and extending generally transverse to a longitudinal axis of said apparatus, said platform including structure for connection to a spinal fixation implant; and at least one helical spike for embedding into the bone upon rotation of said platform, said at least one helical spike projecting tangentially from said first surface of said platform and extending around said longitudinal axis, said at least one helical spike having a proximal end and a distal end;

said at least one helical spike including a tip portion at said distal end which penetrates into the bone as said platform is rotated, a connecting portion at said proximal end connected to said first surface of said platform, and an intermediate portion extending between said connecting portion and said tip portion;

at least one of said intermediate portion and said connecting portion of said at least one helical spike having a tubular cross-section defined by an outer diameter and an inner diameter of said at least one helical spike.

2. The apparatus of claim 1 wherein said connecting portion of said at least one helical spike has a first outer diameter and said intermediate portion of said at least one helical spike has a second outer diameter that is less than said first outer diameter.

3. The apparatus of claim 1, wherein said connecting portion of said at least one helical spike has a first outer diameter and said intermediate portion of said at least one helical spike has a second outer diameter that is equal to said first outer diameter.

4. The apparatus of claim 1 wherein said outer diameter of said at least one helical spike has a first radius and said inner diameter of said at least one helical spike has a second radius, said second radius being less than said first radius;

said connecting portion of said at least one helical spike having a first wall thickness defined between said first radius and said second radius, said intermediate portion of said at least one helical spike having a second wall thickness defined between said first radius and said second radius.

5. The apparatus of claim 4 wherein said first wall thickness of said connecting portion is greater than said second wall thickness of said intermediate portion.

6. The apparatus of claim 4 wherein said first wall thickness of said connecting portion is equal to said second wall thickness of said intermediate portion.

7. The apparatus of claim 1 wherein said intermediate portion of said at least one spike has a tubular cross-section and at least one of said connecting portion and said tip portion has a solid cross-section.

8. The apparatus of claim 1 comprising a pair of helical spikes extending around said longitudinal axis, said proximal ends of said pair of helical spikes being spaced 180° apart.

9. The apparatus of claim 1 comprising three helical spikes extending around said longitudinal axis, said proximal ends of said helical spikes being spaced 120° apart.

10. The apparatus of claim 1 wherein said first surface has a shape that is complimentary to the shape of an outer surface of the bone for engaging the outer surface of the bone.

11. The apparatus of claim 1 wherein said tip portion of said at least one helical spike has an elongated conical shape with a sharp pointed tip that penetrates into the bone as said platform is rotated.

12. The apparatus of claim 1 wherein said tip portion of said at least one helical spike has a self-penetrating terminal end that includes a planar surface for driving into the bone as said platform is rotated.

13. An apparatus comprising:

at least one anchor for implantation into a bone, said at least one anchor having a longitudinal axis, when implanted, being resistant to toggling in the bone and to being pulled from the bone; and a spinal fixation implant for extending between and connecting a plurality of bones;

said at least one anchor including a platform having a first surface for facing the bone, said first surface being solid and extending generally transverse to said longitudinal axis, said platform further having structure for connection with said spinal fixation implant;

said at least one anchor further including at least two helical spikes for embedding into the bone upon rotation of said platform, said at least two helical spikes projecting tangentially from said first surface on said platform and extending around said longitudinal axis, each of said at least two helical spikes having a proximal end and a distal end;

each of said at least two helical spikes including a tip portion at said distal end which penetrates into the bone as said platform is rotated, a connecting portion at said proximal end connected to said first surface of said platform, and an intermediate portion extending between said connecting portion and said tip portion;

at least one of said intermediate portion and said connecting portion of each of said at least two helical spikes having a tubular cross-section defined by an outer diameter and an inner diameter of said at least two helical spikes.

14. The apparatus of claim 13 wherein said connecting portion of each of said at least two helical spikes has a first outer diameter and said intermediate portion of each of said at least two helical spikes has a second outer diameter that is less than said first outer diameter.

15. The apparatus of claim 13 wherein said connecting portion of each of said at least two helical spikes has a first outer diameter and said intermediate portion of each of said at least two helical spikes has a second outer diameter that is equal to said first outer diameter.

16. The apparatus of claim 13 wherein said outer diameter of each of said at least two helical spikes has a first radius and said inner diameter of each of said at least two helical spikes has a second radius, said second radius being less than said first radius;

said connecting portion of each of said at least two helical spikes having a first wall thickness defined between said first radius and said second radius, said intermediate portion of each of said at least two helical spikes having a second wall thickness defined between said first radius and said second radius.

17. The apparatus of claim 16 wherein said first wall thickness of said connecting portion of each of said at least two helical spikes is greater than said second wall thickness of said intermediate portion of each of said at least two helical spikes.

18. The apparatus of claim 16 wherein said first wall thickness of said connecting portion of each of said at least two helical spikes is equal to said second wall thickness of said intermediate portion of each of said at least two helical spikes.

19. The apparatus of claim 13 wherein said intermediate portion of said at least one spike has a tubular cross-section and at least one of said connecting portion and said tip portion has a solid cross-section.

20. The apparatus of claim by wherein said proximal ends of said at least two helical spikes are spaced 180° apart.

21. The apparatus of claim 13, wherein said at least one anchor has three helical spikes extending around said longitudinal axis, said proximal ends of said three helical spikes being spaced 120° apart.

22. The apparatus of claim 13 wherein said first surface has a shape that is complimentary to the shape of an outer surface of the bone for engaging the outer surface of the bone.

23. The apparatus of claim 13 wherein said tip portion of each of said at least two helical spikes has an elongated conical shape with a sharp pointed tip that penetrates into the bone as said platform is rotated.

24. The apparatus of claim 13 wherein said tip portion of each of said at least two helical spikes has a self-penetrating terminal end that includes a planar surface for driving into the bone as said platform is rotated.

25. The apparatus of claim 13 comprises a first anchor for implantation into a first bone and a second anchor for implantation into a second bone spaced from said first bone.

26. The apparatus of claim 23 wherein each of said first and second anchors extends co-linearly along said longitudinal axis, said at least two helical spikes that project from said platform of said first anchor extending in a first direction, said at least two helical spikes that project from said platform of said second anchor extending in a second direction opposite said first direction.

27. The apparatus of claim 26 wherein said spinal fixation implant comprises a member extending along said longitudinal axis and interconnecting said first and second anchors.

28. An apparatus for implantation into an adjacent pair of vertebral bodies having first and second surfaces that oppose each other, said apparatus, when implanted, being attached to each of the vertebral bodies and stabilizing the vertebral bodies while the vertebral bodies fuse together, said apparatus comprising:
- a platform having a third surface extending generally transverse to a longitudinal axis of said apparatus; and
- at least two helical spikes for embedding into each of the adjacent pair of vertebral bodies upon rotation of said platform to attach said at least two helical spikes to each of the vertebral bodies and thus fasten the vertebral bodies together, said at least two helical spikes projecting tangentially from said third surface of said platform and extending around said longitudinal axis;
- each of said at least two helical spikes having a tip portion at a distal end for penetrating the first and second surfaces and for screwing into the adjacent pair of vertebral bodies as said platform is rotated;
- at least a portion of each of said at least two helical spikes having a tubular cross-section defined by an outer diameter and an inner diameter;
- said at least two helical spikes at least partially defining an internal cavity for receiving material that promotes fusion of the vertebral bodies.

29. The apparatus of claim 28 wherein said tip portion of each of said at least two helical spikes has a self-penetrating terminal end for penetrating into the bone as said platform is rotated.

30. The apparatus of claim 28 wherein said apparatus comprises a pair of helical spikes extending around said longitudinal axis, said proximal ends of said helical spikes being spaced 180° apart.

31. The apparatus of claim 28 wherein said apparatus comprises three helical spikes extending around said longitudinal axis, said proximal ends of said helical spikes being spaced 120° apart.

32. The apparatus of claim 28 wherein said platform includes structure for connection to a spinal fixation implant.

33. The apparatus of claim 28 wherein each of said at least two helical spikes has a connecting portion at a proximal end connected to said platform and an intermediate portion extending between said connecting portion and said tip portion.

34. The apparatus of claim 33 wherein said intermediate portion of each of said at least two helical spikes has a first outer diameter and said connecting portion of each of said at least two helical spikes has a second outer diameter that is greater than said first outer diameter.

35. The apparatus of claim 33 wherein said intermediate portion of each of said at least two helical spikes has a first outer diameter and said connecting portion of each of said at least two helical spikes has a second outer diameter that is equal to said first outer diameter.

36. The apparatus of claim 33 wherein said outer diameter of each of said at least two helical spikes has a first radius and said inner diameter of each of said at least two helical spikes has a second radius, said second radius being less than said first radius;
- said connecting portion of each of said at least two helical spikes having a first wall thickness defined between said first radius and said second radius, said intermediate portion of each of said at least two helical spikes having a second wall thickness defined between s aid first radius and said second radius.

37. The apparatus of claim 36 wherein said first wall thickness of said connecting portion is greater than said second wall thickness of said connecting portion.

38. The apparatus of claim 36 wherein said first wall thickness of said connecting portion is equal to said second wall thickness of said intermediate portion.

39. The apparatus of claim 33 wherein said intermediate portion of each of said at least two spikes has a tubular cross-section and at least one of said connecting portion and said tip portion has a solid cross-section.

40. The apparatus of claim 28 wherein said platform includes an axially extending passage through which the material is placed into said internal cavity following implantation of said apparatus in the vertebral bodies.

* * * * *